United States Patent [19]

Creekmore et al.

[11] Patent Number: 5,693,322

[45] Date of Patent: Dec. 2, 1997

[54] ENHANCED INTERCELLULAR INTERACTION BY ASSOCIATIONAL ANTIBODY MOLECULES

[75] Inventors: Stephen P. Creekmore, Frederick; Toby T. Hecht, Bethesda; John Ortaldo, Frederick, all of Md.

[73] Assignee: The United States of America as represented by the Department of Health and Human Services, Washington, D.C.

[21] Appl. No.: 30,843

[22] Filed: Mar. 11, 1993

[51] Int. Cl.$^6$ .......................... C07K 16/28; C07K 16/30
[52] U.S. Cl. .................. 424/138.1; 424/144.1; 424/130.1; 530/387.5; 530/387.7; 530/388.73; 530/388.8; 530/391.1
[58] Field of Search ................ 424/85.8, 138.1, 424/144.1; 530/387.5, 387.7, 388.73, 388.8, 391.1; 435/240.27, 70.21, 172.2

[56] References Cited

U.S. PATENT DOCUMENTS

| 4,444,744 | 4/1984 | Goldenberg . |
| 4,849,509 | 7/1989 | Thurin et al. ................ 530/387.5 |
| 5,078,998 | 1/1992 | Bevan et al. . |
| 5,104,652 | 4/1992 | Houghton et al. . |

FOREIGN PATENT DOCUMENTS

WO 9210209  12/1991  WIPO .

OTHER PUBLICATIONS

Kimmel et al., J. Neurosurg 66:161–171, 1987.
Waldman, Science 252:1657–1662, 1991.
Hird et al. in Carney et al. Eds "Genes and Cancer," 1990, John Wiley & Sons, pp. 183–189.
Harris et al. Tibtech 11:42–44, 1993.
Osband et al. Immunology Today 11: 193–195, 1990.
Cheresh et al. Cancer Res. 46:5112–5118, 1986.
Schlom, in:"Molecular Foundertions of Oncology" Bodes, ed., Williams & Wilkins 1991, pp. 98–134.
Welt, Sydney et al. *Clinical Immunology and Immunopathology;* "Immune and Nonimmune Effector Functions of IgG3 Mouse Monoclonal Antibody R24 Detecting the Disialoganglioside GD3 on the Surface of Melanoma Cells"; 45:214–229 (1987).
Welte, Karl et al. Journal of Immunology; "Stimulation of T Lymphocyte Proliferation by Monoclonal Antibodies Against $G_{D3}$ Ganglioside"; 139:1763–1771 (Sep. 15, 1987).
Morgan, Alton C. Jr. et al *Biological Abstracts* "Murine Monoclonal IgG3 to Human Colorectal Tumor–Associated Antigenes: Enchancement of Antibody–dependent cell–mediated cytotoxicity by Interlenkin–2"; 88 (2) :Abstract 17623 (1989).
Pack, Peter et al. *Biochemistry;* "Miniantibodies: Use of Amphipathic Helices to Produce Functional, Flexibly Linked Dimeric $F_v$ Fragments with High Avidity in *Escherichia coli*"; 31:6, pp. 1579–1584 (1992).

Greenspan, Neil S. et al. Immunology Today; "Intermolecular cooperativity: a clue to why mice have IgG3?"; 13:5 pp. 164–168 (1992).
Abdelmoula et al., *J. Immunol.;* "IgG3 is the Major Source of Cryoglobulins in Mice"; 143:526–532 1989.
Berney et al., *J. Immunol.;* "Murine Cryoglobulinemia: Pathogenic and Protective IgG3 Self–Associating Antibodies"; 147:3331–3335 1991.
Canfield et al., *J. Exp. Med.;* "The Binding Affinity of Human IgG for its High Affinity Fc Receptor Is Determined by Multiple Amino Acids in the $C_H2$ Domain and Is Modulated by the Hinge Region"; 173:1483–1491 1991.
Chapman et al., *J. Immunol.;* "Homophilic Binding of Mouse Monoclonal Antibodies Against $G_{D3}$ Ganglioside"; 145:891–898 1990.
Cohen et al., *J. Immunol. Methods;* "Production and Characterization of Monoclonal Antibodies Against Human Glycoalbumin"; 117:121–129 1989.
Creekmore et al.; *Proceedings of Asco;* "PhaseIB/II Trial of R24 Antibody and Interleukin–2 (IL2) in Melanoma"; 11:345 Mar. 1992.
Ehrlich et al.; *J. Immunol.;* "Mixing Two Monoclonal Antibodies Yields Enhanced Affinity for Antigen"; 128:2709–2713 1982.
Garrido et al., *Cancer Research;* "Targeting Human T–Lymphocytes with Bispecific Antibodies to React Against Human Ovarian Carinoma Cells Growing in nu/nu Mice"; 50:4227–4232 1990.
Greenspan et al.; *J. Immunol.;* "Fc Region–Dependence of IgG3 Anti–Streptococcal Group A Carbohydrate Antibody Functional Affinity"; 141:4276–4282 1988.
Greenspan et al., *J. Immunol.;* "Interaction of IgG3 Anti–Streptococcal Group A Carbohydrate (GAC) Antibody with Streptococcal Group A Vaccine: Enhancing and Inhibiting Effects of Anti–GAC, Anti–Isotypic, and Anti–Idiotypic Antibodies"; 138:285–292 1987.
Greenspan et al., *FASEB Journal;* "Cooperative Binding of Two Antibodies to Independent Antigens by a Fc–Dependent Mechanism"; 3:2203–2207 1989.
Grey et al., *Scripps Clinic and Research Foundation* (1970); "A New Mouse Immunoglobulin: IgG3"; pp. 289–304.
Houghton et al., *Proc. Natl. Acad. Sci. USA;* "Mouse Monoclonal IgG3 Antibody Detecting $G_{D3}$ Ganglioside: A Phase I Trial in Patients with Malignant Melanoma"; 82:1242–1246 1985.
Snapper et al., *J. Exp. Med.;* "Induction of IgG3 Secretion by Interferon µ: A Model for T Cell–Independent Class Switching in Response to T Cell–Independent Type 2 Antigens"; 175:1367–1371 1992.

(List continued on next page.)

*Primary Examiner*—Toni R. Scheiner
*Attorney, Agent, or Firm*—Knobbe, Martens, Olson & Bear LLP

[57] ABSTRACT

A method to enhance intercellular association between two or more cells through the linking of attachment molecules on the cellular surfaces of the cells is described. Appropriate attachment molecules include antibodies having an $IgG_3$ isotype that can cross-associate with antibodies on other cells to bring the cells into proximity with one another. An enhanced method to kill tumor cells with effector cells is also provided.

28 Claims, 7 Drawing Sheets

OTHER PUBLICATIONS

Snapper et al., *Immunol. Today;* "Towards a Comprehensive View of Immunoglobulin Class Switching"; 14:15–17 1993.

Spertini et al., *Eur. J. Immuno.* (1989); "Inhibition of Cryoprecipitation of Murine IgG3 Antidinitrophenyl (DNP) Monoclonal Antibodies by Anionic DNP–Amino Acid Conjugates"; 19:273–278 1989.

Steplewski et al., *Proc. Natl. Acad. Sci. USA;* "Biological Activity of Human–Mouse IgG1, IgG2, IgG3, and IgG4 Chimeric Monoclonal Antibodies with Antitumor Specificity"; 85:4852–4856 1988.

Sun et al., *Proc. Natl. Acad. Sci. USA;* "Chimeric Antibody with Human Constant Regions and Mouse Variable Regions Directed Against Carcinoma–Associated Antigen 17–1A"; 84:214–218 1987.

Wels et al., *EMBO Journal;* "Structural Analysis of the Murine IgG3 Constant Region Gene"; 3:2041–2046 1984.

Deborah Illman, *C&EN;* "Polymer Mimics Antibody in Drug Assay"; Mar. 1, 1993, pp. 30–31.

Kostelny et al., *J. Immunol.;* "Formation of a Bispecific Antibody by the Use of Leucine Zippers"; 148:1547–1553.

Luzuy et al., *J. Immunol.;* "Autoimmunity After Induction of Neonatal Tolerance to Alloantigens: Role of B Cell Chimerism and F1 and Donor B Cell Activation"; 136:4420–4426.

O'Shea et al., *The New Biologist;* "Killer T's, Macrophages, and NK's"; 2:779–782.

Perlmutter et al., *J. Immunol.;* "Subclass Restriction of Murine Anti–Carbohydrate Antibodies"; pp. 566–572, vol. 121 (1978).

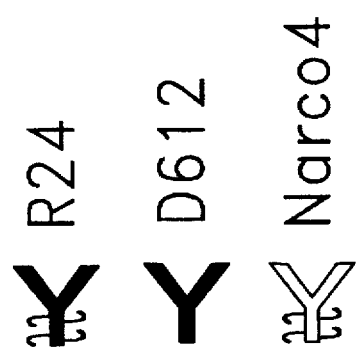
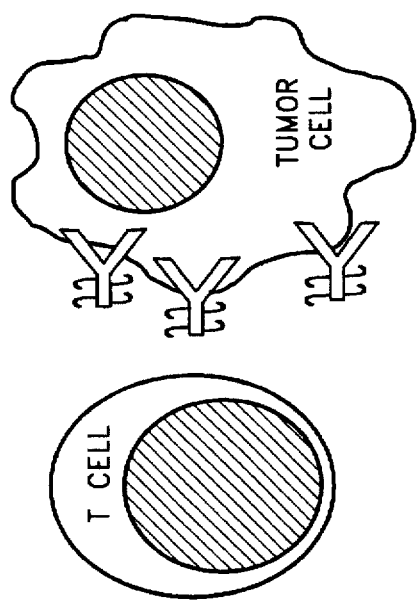
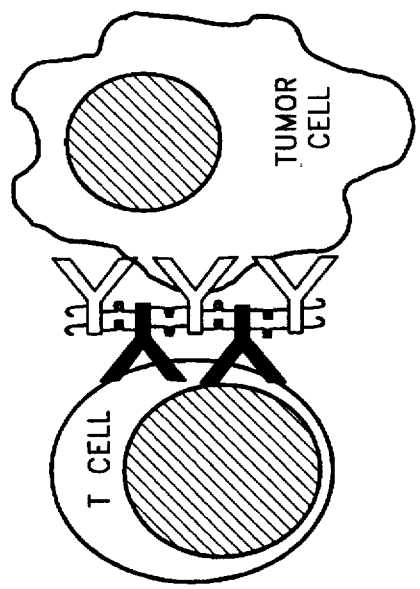
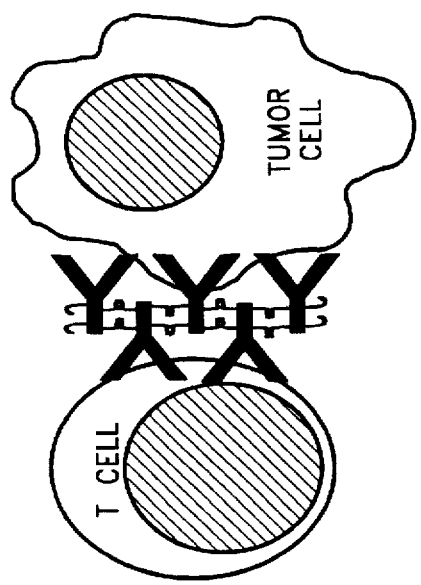
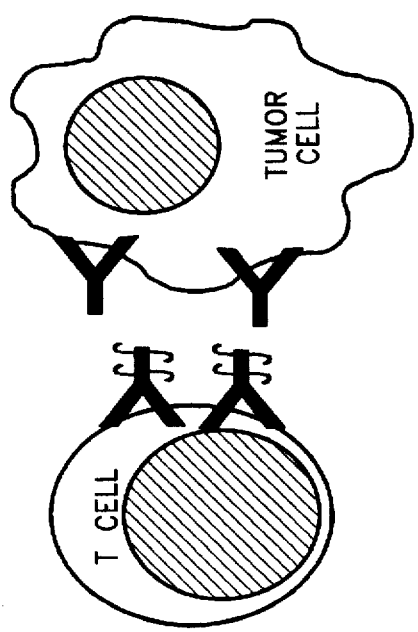
FIG. 6A  FIG. 6B  FIG. 6C  FIG. 6D

ENHANCED INTERCELLULAR INTERACTION BY ASSOCIATIONAL ANTIBODY MOLECULES

BACKGROUND OF THE INVENTION

1. Field of the Invention

The present invention relates to a method of enhancing the intercellular interaction between two or more cells, thereby providing an enhanced method of killing tumor cells with human effector cells, such as lymphocytes. More specifically, the method relates to the use of associational molecules, such as antibodies with an associational domain, that are targeted to the cellular surface.

2. Background of the Art

As early as 1971, it was noted that the $F_c$ portion of murine $IgG_3$ antibodies had the property of self-association, particularly at low temperatures and at low salt concentrations. Grey, H. M., et al. *J. Exp. Med.*, 133:289–304 (1971). In their studies of $IgG_3$ monoclonal antibodies, Greenspan and colleagues demonstrated that murine $IgG_3$'s specific for sugar residues on the streptococcal group A surface would cooperatively bind to solid phase natural or synthetic antigens through an $F_c$ region-dependent mechanism. Greenspan, N. S., et al. *J. Immunol.*, 138:285–292 (1987); Greenspan, N. S. et al. *J. Immunol.*, 141:4276–4282 (1988).

In contrast, however, F(ab')$_2$ fragments did not have the ability to cooperatively bind. In later studies, it was shown that $IgG_3$ monoclonal antibodies, but not antibodies of other isotypes, also demonstrated cooperative binding. Greenspan, N. S., et al. *FASEB J.*, 3:2203–2207 (1989); Berney, T. et al. *J. Immunol.*, 147:3331–3335 (1991).

It was postulated, therefore, that $F_c$—$F_c$ non-covalent associations would increase the functional affinity (avidity) of an antibody for its target thereby increasing the equilibrium association constant of the antibody binding. Thus, it was proposed that the cooperative binding of $IgG_3$ antibodies offered a new strategy for diagnosis and therapy by enhancing the avidity of complexed antibodies for their target cells. Greenspan, N. S. et al. *J. Immunol.*, 141:4276–4282 (1988).

Moreover, it was suggested that it may be possible, through genetic engineering, to confer on non-antibody proteins, such as receptor ligands, the ability to engage in cooperative intermolecular interactions. Id.

In another aspect of the art, lymphocyte directed killing of cells, such as tumor cells, has been extensively researched and documented. E.g., O'Shea, J. J., et al. *The New Biologist*, 2:779–782 (1990). The effect of lymphocyte directed killing of tumor cells is often enhanced by the inclusion of an antibody.

$IgG_3$ mAb's predominate in the murine immune response to various bacterial polysaccharide antigens. Greenspan et al. *FAESB*, 3:2203–2207 (1989); Permutter et al. *J. Immunol.*, 121:566 (1978). Recent reports have indicated that cooperativity between murine $IgG_3$ molecules may represent a novel mechanism for increasing antibody avidity and may help explain the preferential emergence of these antibodies in their interactions with bacteria expressing carbohydrate antigens. The possibility that $F_c$—$F_c$ interactions may account for $IgG_3$ cooperativity is supported by data demonstrating that murine $F_c$3 regions self-aggregate in vitro. Greenspan et al. *FAESB*, 3:2203–2207 (1989). R24$_{\gamma 3}$ represents a mAb of the $IgG_3$ isotype that binds to the disialoganglioside (GD3) antigen present on melanoma cells, as well as binding to a subset of T cells. The R24$_{\gamma 3}$ producing hybridoma cell line is deposited with the American Type Culture Collection, Rockville, Md., as ATCC Deposit No. HB 8445.

In phase I clinical trials, R24$_{\gamma 3}$ administration to patients with melanoma expressing a GD3 resulted in significant clinical responses. Houghton et al. *Proc. Natl. Acad. Sci. (USA)* 82:1242–1246 (1985). In other phase I clinical trials, objective responses have been observed in melanoma patients treated with R24$_{\gamma 3}$ plus IL-2, when the IL-2 was given before the antibody administration (Creekmore S., et al., Phase Ib/II Trial of R24$_{\gamma 3}$ Antibody and Interleukin-2 (IL-2) in Melanoma, *Proc. ASCO*, 4:1186, 1992). IL-2 given subsequent to the R24$_{\gamma 3}$ administration resulted in no significant, objective clinical responses. Sznol M., *Unpublished Observations*. The possibility exists that some objective clinical responses observed may have been the result of an R24$_{\gamma 3}$-mediated bridging between effector and target cells.

Non-MHC (major histocompatibility complex) restricted cytotoxicity can be mediated by numerous lymphocyte subsets including natural killer (NK) cells, CD4$^+$ and CD8$^+$ T cells expressing either an $\alpha/\beta$ or an $\gamma/\delta$ cell receptor. Cells may mediate cytotoxicity in the absence of major histocompatibility complex ("MHC") restriction by using combinations of receptor ligand interactions. Many of the recent studies with redirected T-cells have used bifunctional antibodies or chemically cross-linked heterobifunctional antibodies containing one binding site able to recognize tumor target moieties and one binding site specific for a T-cell receptor-triggering molecule like CD3.

Unfortunately, bifunctional agents typically bind their targets in 1:1 molecular ratios. In many cases, however, antigen density may be much higher on one or the other cell types being targeted. Also, clinicians may want to target more than one antigen on a cell type. It would provide a great advantage to have a method of interacting two cell types wherein the clinician could choose the molecular ratios of effector cells to target cells. Additionally, it would provide an advantage to have a method of interacting two cell types wherein multiple antigens on the cell surface could be targeted.

SUMMARY OF THE INVENTION

The present invention relates to a method of enhancing intercellular interaction between two or more cells through associational molecules targeted to the cellular surface. Appropriate associational molecules include antibodies that contain an associational domain which has affinity for antibodies bound to other cell surfaces. This method can be used to bring normal non-associating cells into proximity with one another. The method also provides an enhanced method of killing tumor cells with human effector cells, such as lymphocytes.

In accordance with a first aspect of the present invention, there is provided a method to facilitate effector cell-directed tumor cell death in a mammal, comprising administering a first antibody specific for a tumor cell antigen to the mammal, the first antibody having a first associational domain, and administering a second antibody specific for a cytotoxic effector cell to the mammal, the second antibody having a second associational domain, wherein the first and second associational domains interact non-covalently to bring the tumor cells in proximity to the effector cell, thereby facilitating cytotoxic effector cell action on the tumor cells.

In a preferred embodiment, each of the first and second associating antibodies are murine $IgG_3$ antibodies. In another preferred embodiment, the effector cell is selected from the group consisting of B-cells, T-cells, non-B and non-T cell lymphocytes, NK cells granulocytes, eosinophils, and monocyte/macrophages. In an even more preferred embodiment, the effector cell is a T-cell.

In other preferred embodiments, an equimolar ratio of the first associating antibody and the second associating antibody are employed. This allows a conventional 1:1 ratio to be used. However, in a highly preferred embodiment, a non-equimolar ratio of the first associating antibody and the second associating antibody are employed. Such a non-equimolar ratio advantageously allows enhanced affinity or association between the effector cell and the tumor cell.

In yet another preferred embodiment, the method further comprises, prior to administering the second antibody, the additional step of administering a effector cell stimulating factor under conditions that promote the growth and propagation of effector cells. The choice of the effector cell stimulating factor is dependent upon the choice of the effector cell target that binds with the second antibody. In preferred embodiments, the effector cell stimulating factor is selected from the group consisting of IL-1, IL-2, IL-3, IL-4, IL-5, IL-6, IL-7, IL-8, IL-9, IL-10, IL-11, IL-12, IL-13, Interferon-α, Interferon-β, Interferon-γ, granulocyte colony stimulating factor, granulocyte-macrophage colony stimulating factor, and monocyte colony stimulating factor.

In accordance with another aspect of the present invention, there is provided a method to facilitate effector cell-directed tumor cell death in a patient having a tumor and bearing a tumor cell antigen, comprising isolating and separating cytotoxic effector cells from the patient, culturing the effector cells under conditions that promote the propagation of the effector cells, administering a first antibody directed against the cytotoxic effector cell culture to the patient, the antibody having affinity for the cytotoxic effector cells and additionally possessing first associational domain, administering to the patient a second antibody specific for the tumor cell antigen in the patient, the second antibody having a second associational domain, and administering to the patient the cultured effector cells, wherein the first and second associational domains interact to bring the tumor cells in proximity to the effector cells, thereby facilitating cytotoxic effector cell action on the tumor cells.

In a preferred embodiment, each of the first and second associating antibodies are murine IgG$_3$ antibodies. In another preferred embodiment, the effector cell is selected from the group consisting of B-cells, T-cells, non-B and non-T cell lymphocytes, NK cells granulocytes, eosinophils, and monocyte/macrophages. In a highly preferred embodiment, the effector cell is a T-cell.

In preferred embodiments, an equimolar ratio of the first associating antibody and the second associating antibody are employed. This allows a conventional 1:1 ratio to be used. However, in a highly preferred embodiment, a non-equimolar ratio of the first associating antibody and the second associating antibody are employed. Such a non-equimolar ratio advantageously promotes enhanced affinity or association between the effector cell and the tumor cell.

In another preferred embodiment, the method further comprises, prior to administering the second antibody, the additional step of administering to the culture an effector cell stimulating factor under conditions that will promote growth and propagation of the effector cells in culture. The choice of the effector cell stimulating factor is dependent upon the choice of the effector cell that binds to the second antibody. In preferred embodiments, the effector cell stimulating factor is selected from the group consisting of IL-1, IL-2, IL-3, IL-4, IL-5, IL-6, IL-7, IL-8, IL-9, IL-10, IL-11, IL-12, IL-13, Interferon-α, Interferon-β, Interferon-γ, granulocyte colony stimulating factor, granulocyte-macrophage colony stimulating factor, and monocyte colony stimulating factor.

In accordance with another aspect of the present invention, there is provided a method to facilitate effector cell-directed tumor cell death in an animal with a tumor, comprising administering to the animal an antibody with an IgG$_3$ isotype heavy chain constant region, having a variable region that is specific for the tumor, and administering monoclonal antibody R24$_{/3}$ to the animal.

In accordance with another aspect of the present invention, there is provided a pharmaceutical kit to facilitate effector cell directed tumor cell death in an animal, comprising a first antibody specific for a tumor cell antigen, the first antibody having a first associational domain, and a second antibody specific for a cytotoxic effector cell, the second antibody having a second associational domain, the first and second associational domains being capable of promoting non-covalent interaction between the first associational domain bound to a tumor cell and the second associational domain bound to a effector cell.

The kit may optionally include providing the first and second antibody in a first and second container. In a highly preferred embodiment, each of the first and second antibody are packaged in their respective containers together with pharmaceutically acceptable buffers, diluents, and/or excipients. Optimally, the kit is packaged together with instructions of how to administer the respective antibodies.

In accordance with another aspect of the present invention, there is provided a method for associating cells, comprising reacting a first associating antibody specific to an antigen on a first cell to the first cell under conditions wherein the first antibody binds to the first cell to form a first antibody-cell conjugate, reacting a second associating antibody specific to a second antigen on a second cell to the second cell under conditions wherein the second antibody binds to the second cell to form a second antibody-cell conjugate, and exposing the first antibody-cell conjugate to the second antibody-cell conjugate, wherein the first and second antibody-cell conjugates become non-covalently associated.

In accordance with another aspect of the present invention, there is provided a method for associating cells, comprising contacting and binding a first antibody to a first cell, the first antibody having a first antigen epitopic domain and a first associational domain, and contacting and binding a second antibody to a second cell, the second antibody having a second antigen epitopic domain and a second associational domain, wherein the first associational domain and the second associational domain associate non-covalently to bring the first and second cell in proximity.

As to each of the methods, in preferred embodiments, the cells are associated in vitro. In another preferred embodiment, each of the first and second conjugating antibodies are murine IgG$_3$ antibodies. In yet another preferred embodiment, the first cell is a tumor cell, and the second cell is a effector cell. Preferably, the effector cell is selected from the group consisting of granulocytes, B-cells, NK cells, T-cells, non-B and non-T cell lymphocytes, eosinophils, and macrocyte/macrophages, and in a highly preferred embodiment, the effector cell is a T-cell. As discussed above, either equimolar ratios or non-equimolar ratios of the first associating antibody and the second associating antibody are employed.

BRIEF DESCRIPTION OF THE DRAWINGS

FIG. 1A illustrates the association between an $IgG_3$ tumor specific antibody and a T-cell specific $IgG_3$ antibody. FIG. 1B illustrates the non-associational effect that results when a T cell is targeted with a non-$IgG_3$ antibody and a tumor cell is targeted with an $IgG_3$ antibody. FIG. 1C illustrates the non-associational interaction that occurs when a T cell is targeted with an $IgG_3$ antibody and a tumor cell is targeted with a non-$IgG_3$ antibody.

FIG. 2A illustrates the association between an $IgG_3$ tumor specific antibody and a T-cell specific $IgG_3$ antibody. FIG. 2B shows the enhanced cross-associational effects possible through use of two tumor-specific $IgG_3$ antibodies to two antigens on the tumor cell. FIG. 2C depicts the blocking effect possible through pretreatment with a non-$IgG_3$ antibody specific for normal tissue that has a tumor antigen on its cell surface prior to administration of an $IgG_3$ tumor specific antibody.

FIG. 6 is a schematic representation of the cross-associational properties of antibodies against effector and target cells. Panel A illustrates the cross-associational effects of the antibody $R24_{\gamma 3}$ on both the effector and target cell; Panel B illustrates the lack of cross-associational effects of the antibody NR-CO4, which binds only to target cells; Panel C illustrates the lack of cross-associational effect of the antibody $R24_{\gamma 3}$ on the effector cell and the antibody D612 on the tumor cell; Panel D illustrates the complete association of the antibody $R24_{\gamma 3}$ on the effector cell and the antibody NR-CO4 on the target cell.

DETAILED DESCRIPTION OF THE PREFERRED EMBODIMENTS

The present invention is related to the discovery that associating molecules, such as antibodies, may be bound to cell surfaces as part of a method for providing interactions between different cell types. Thereafter, when cells having the associating molecules attached are exposed to one another, they can interact leading to advantageous in vivo and in vitro results.

An "associating molecule" is used herein to describe any molecule that when bound to a cell on the cell surface, possesses a region which permits the molecule to form an association with a second associating molecule also bound to a cell. An example of an associating molecule, in a preferred embodiment of the present invention, is a murine $IgG_3$ monoclonal antibody. Thus, a preferred associating molecule is an "associating antibody". It will be appreciated that such antibodies comprise two heavy chains and two light chains, each chain of which contains a variable region, that is ordinarily immunospecific for certain antigens, and a constant region. The variable region of the antibody can be thought of as lying flat or relatively flat on the cell surface, forming the top bar of a "T" or a notch of a "Y".

The constant region of an antibody extends from the end of the variable region away from the cellular surface, and in the heavy chain, the constant region extends some distance away from the cellular surface, similar to the tail of a "T" or "Y". It will be appreciated that $IgG_3$ constant regions are known to self-associate.

Antibody self-association is a phenomenon where the constant region of an antibody associates with other, similar, constant regions on either the same antibody or a similar antibody. For the sake of simplicity, and not wishing to be bound to any particular theory, it can be imagined that a first $IgG_3$ antibody is bound to an antigen on a first cell. A second, similar $IgG_3$, located on the same cell type, associates with the first antibody. Thus, the two constant region tails extend from the cellular surface and interact through non-covalent binding.

Thus, in order to ensure that appropriate cells become associated, an $IgG_3$ monoclonal antibody having specificity for particular cellular antigens is chosen. For example, in a preferred embodiment, an $IgG_3$ antibody specific for a tumor cell antigen is selected as a first antibody and an $IgG_3$ antibody specific for a particular effector cell is selected as a second antibody.

In such an embodiment, the antibody for the tumor antigen will localize at any tumor cell bearing the target antigen. Similarly, the antibody with affinity for the effector cell will localize at the particular effector cell having a target antigen. When this occurs, the associating properties of the antibodies will cause the cells to associate, bringing them in proximity to one another. Upon this association, the effector cell is positioned to attack the tumor cell and cause, for example, lysis.

Figure 1A:
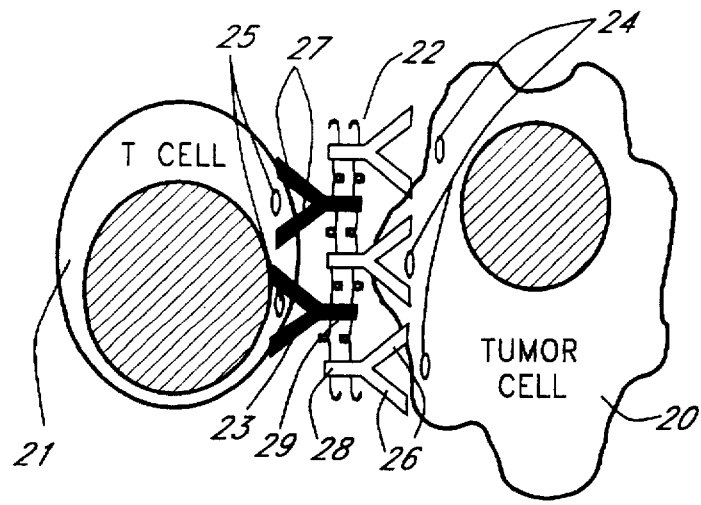
FIGS. 1A–1C represent a series of diagrams illustrating the associational properties of $IgG_3$—$IgG_3$ heavy chain constant regions.

It is believed that this reactivity is enhanced because of the associational domains on the $IgG_3$ antibodies, which are thought to reside in the $Ig_3$ heavy chain constant regions. While not wishing to be bound to a particular theory, referring now to FIGS. 1A–1C, a series of schematic views of this aspect of the present invention is depicted. T-cells are shown interacting with tumor cells, each with antibodies attached to their respective cellular antigens. In FIG. 1A, each of the tumor cell 20 and T-cell 21 have $IgG_3$ antibodies 22 and 23, respectively, bound at antigens 24 (tumor cell) and 25 (T-cell) through their variable regions 26 (tumor specific antibody) and 27 (T-cell specific antigen), respectively that are associating through constant regions 28 (tumor specific antibody) and 29 (T-cell specific antibody).

Figure 1B:
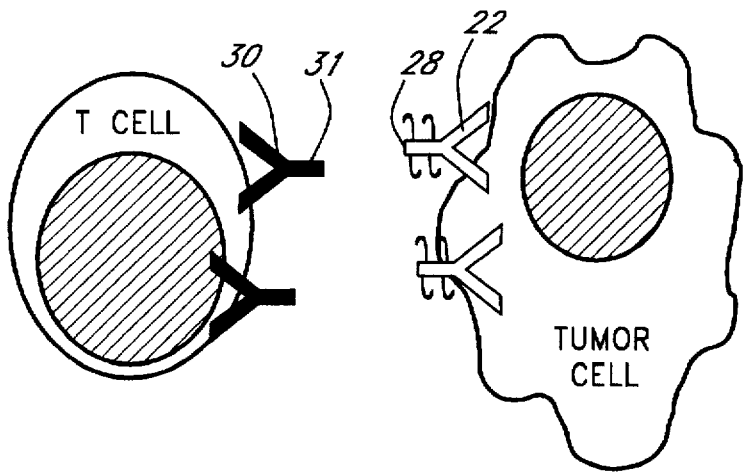
Figure 1C:
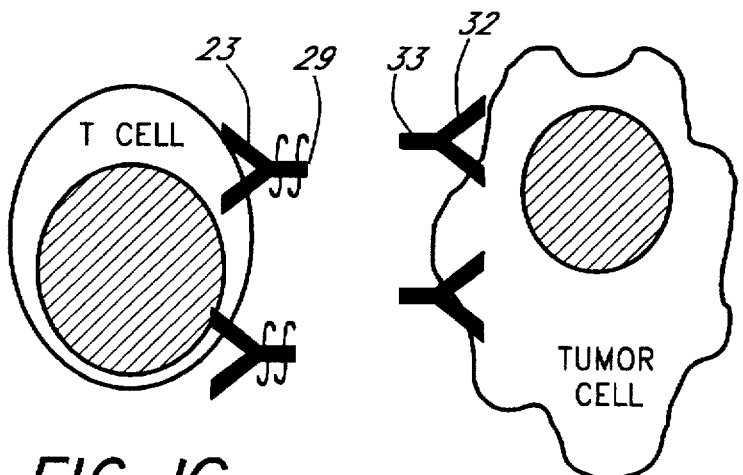

In FIG. 1B, the constant region 28 on the tumor specific antibody 22 is not associative with the constant region 31 on the T-cell specific antibody 30. In this example, the non-associativity arises because the constant region 31 is not an $IgG_3$ isotype. Accordingly, there is no association between the constant regions 31 and 28 of the antibodies. Similarly, in FIG. 1C, the constant region 33 on the tumor specific antibody 32, is not an $IgG_3$ isotype, and, therefore exhibits no association with the constant region 29 on the T cell antibody 23.

Figure 2A:
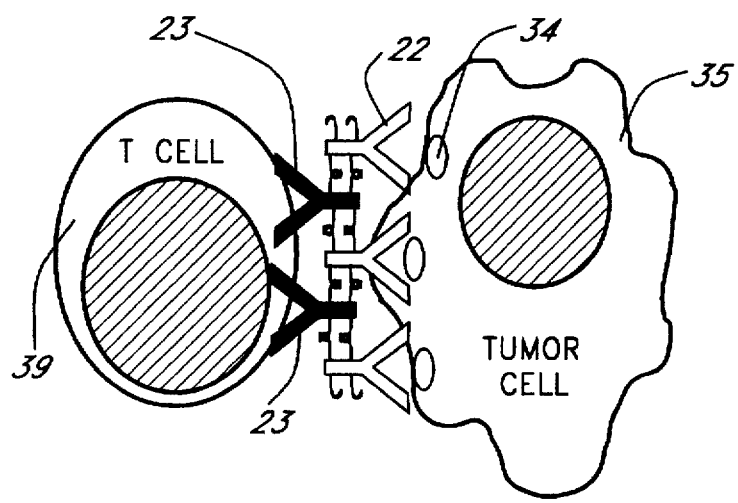
FIGS. 2A–2C represent a series of schematic representations of a preferred embodiment of the present invention illustrating both possible cross-associational or the blocking of cross-associational effects on normal tissue.
Figure 2B:
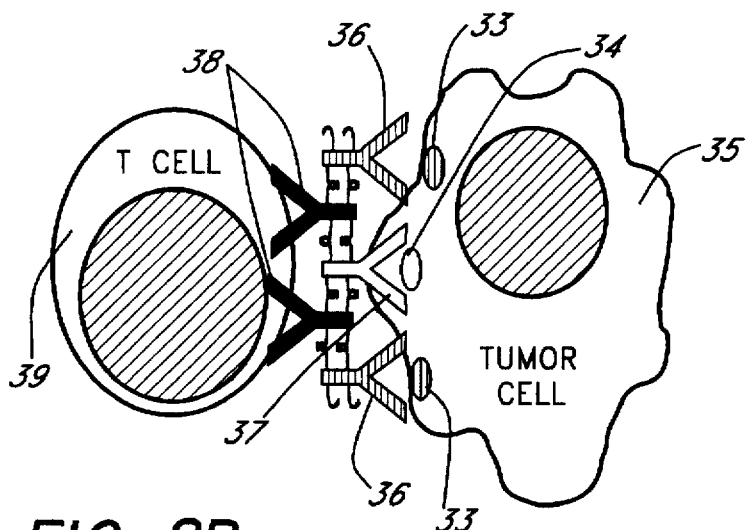

Referring now to FIG. 2, there is provided another schematic representation of one embodiment of the present invention. In FIG. 2A, the same association between a tumor specific $IgG_3$ antibody 23 and an effector cell specific $IgG_3$ antibody 22 is seen as described in FIG. 1A. In FIG. 2B, multiple antigens on a single tumor cell are targeted by associating antibodies. The tumor cell 35 has antigens B1 (34) and B2 (33), each of which are localized by anti-tumor antibodies 36 and 37. Each of the anti-tumor antibodies 36 and 37, through their associational domains can cross-associate with the T-cell antibodies 38, bound to an antigen on the T-cell 39.

Figure 2C:
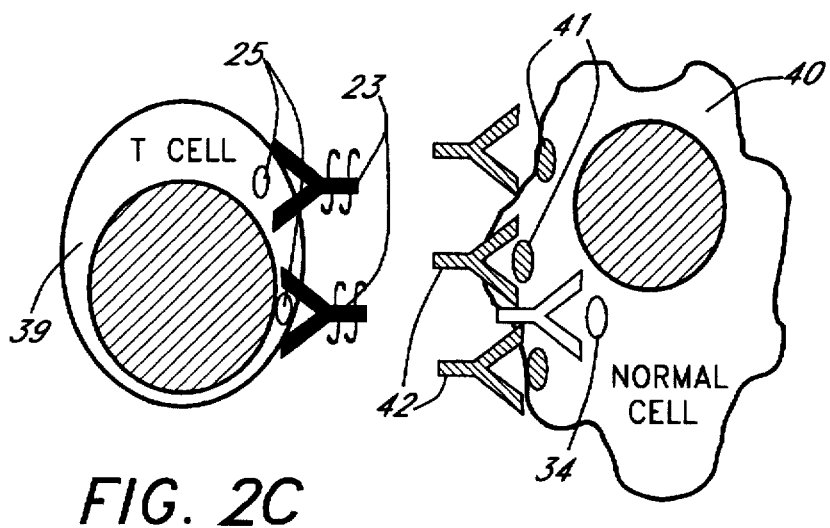

Thus, it will be appreciated that even in tumors with low ratios of accessible antigens, it is expected that strong associational effects can be obtained through the use of multiple antibody/antigen systems on tumor cells, wherein the antibodies have associational domains. Also, it is expected that protection from cross-reactivity between antibodies and antigens that are not selected for can be afforded through the selective use of non-$IgG_3$ antibodies to protect normal tissue cells which happen to bear a tumor antigen or a cross-reacting antigen. In FIG. 2C, it can be seen that the tumor antigen B1 (34) is also present on a normal cell 40. A normal tissue antigen B3 (41) is also present on the normal tissue cell 40. Use of the non-$IgG_3$ antibodies 42 to B3 (41) can be used to provide protection to the normal cells and reduce the likelihood of its destruction by the T-cell 39 having $IgG_3$ antibodies 23 bound to a T-cell antigen 25.

It will be understood that this technique is a particularly advantageous aspect of the present invention. It allows a clinician to first treat a patient with non-associating antibodies specific for the normal tissue antigen B3. Such antibodies will localize at the normal tissues. Thereafter, the clinician can treat the patient with a tumor-specific associating antibody that will localize at tumor tissues in preference to the normal tissue having the tumor antigen B1, since, there will be some blocking of the normal tissues by the non-associating B3 specific antibody. Moreover, even if the anti-B1 associating antibody does localize at the normal tissue, when the associating antibody to the effector cell is administered, the likelihood of effector cell interaction with normal tissue having bound anti-B1 associating antibody is expected to be substantially diminished relative to the interaction that will be seen between the tumor cells with anti-B1 associating antibodies bound to their surfaces.

As will be appreciated, this technique serves a dual role in protecting normal tissue from attack by the activated effector cells. First, the blocking provided by the non-$IgG_3$ antibodies interferes with cross-reactivity between antibodies to the tumor antigen on the normal tissue (B1—B1 cross-reactivity). And, second, the blocking interferes with the cross-reactivity between the $IgG_3$ antibodies on effector cells with normal tissue antigen B3.

The above described novel processes have been demonstrated through in vitro studies in which the effects of monoclonal antibody attachment on effectors and target cells were compared. As explained in more detail below, in vitro studies used monoclonal $IgG_3$ antibodies that were specific for antigens on either effector cells or the target tumor cells. The results demonstrated that the combined effect of one $IgG_3$ antibody specific for the tumor target and another $IgG_3$ antibody specific for the effector cell increased tumor cell lysis by a factor 3 to 8, dependent on antibody concentration. Moreover, the association between tumor and target cells was readily observable microscopically.

Accordingly, it is expected that any molecule that can be bound to a cellular surface and contains an associational or attractive domain could lead to cellular association between cells, and act as an "associational molecule" in accordance with the present invention.

It will be appreciated that the present invention provides a dramatic improvement over the more conventional process of cross-linking cells by heterobifunctional antibodies. Where chemical cross-linking is employed, the cross-linked antibody conjugate binds to the cellular surface using one of its two binding domains. Subsequent binding of the antibody to the other antigen-containing cell is far more sterically hindered due to the cell's dramatically greater mass in comparison to the size of the antibody. In contrast, in the present invention, each antibody is free to bind with its respective antigen prior to the introduction of steric considerations to the binding calculus.

While not wishing to be bound to any particular theory or mode of action, where the associational molecule is an antibody, the large numbers of relatively weak non-covalent interactions between the constant regions of the antibodies are believed to gradually draw the cells together, potentially immobilizing the cells into a cellular conjugate. An analogy for this type of novel intercellular association is a Velcro®-like interaction between cells. However, it is expected that there is a degree of "float" provided between the cells, i.e., if the constant regions are perceived as slidably mounted rods, it will be understood that the cells are able to generally move with respect to one another without affecting the binding between the antibody and its antigen.

The cellular association enabled through the present invention has multiple uses. A particularly preferred use of the present invention is tumor cell lysis by effector cells. It is well established that effector cells, e.g., lymphocytes, can be activated to kill tumor cells, or to secrete factors which may recruit other effector cells to kill the tumor cells.

Several theories have been advanced for these effects, among which, it has been contemplated that the antibodies must act to trigger the effector or the target to produce cytokines. In the alternative, it has been reasoned that the killing may be due to the mere proximity of effector cells and targets. Or, these effects may combine and induce the recruiting or attracting of additional effectors.

Whatever the mode of action, it has been observed that the present invention enhances the cytotoxicity of effector cells. We expect that this enhancement is contributed to by the cross-association accomplished in accordance with the present invention. The present invention provides a convenient and highly effective method to enhance such lysis; apparently driven by the fact that the effector cells will actively associate with tumor cells through the constant region interactions of antibodies or presumably any associating domain.

Further, a similar mechanism also appears to promote the fusion potential between cells. This effect enhances the ability to make, for example, hybridoma cell lines. Also, through associating cells in accordance with the present invention, synergistic effects of cells may be harnessed. For example, it is expected that combinations of cells can be associatively combined in accordance with the present invention so as to secrete desired by-products, i.e., growth factors, stimulating factors, attachment factors, and the like. Such products are known to be produced in mixed cell culture, and thus, their production is expected to be enhanced in accordance with the present invention.

I. CONSTRUCTION OF ASSOCIATIONAL MOLECULES

As mentioned above, an associational molecule in accordance with the present invention is any molecule that allows a specific binding to a particular cell type that further contains a region, away from the cell surface, that allows a non covalent linkage with another associational molecule, preferably, specifically bound to another cell. Moreover, optimally, the second cell is another cell type.

The preferred associational molecule is an antibody, and in a particularly preferred embodiment, the associational molecule is a murine $IgG_3$ monoclonal antibody. It will be understood, that an antibody is preferred, since, antibodies can be readily prepared by those of skill in the art to particular antigens on particular cells. Thus, they provide a convenient binding platform upon which to provide an associational domain.

Interestingly, the spontaneous aggregation of $IgG_3$ antibodies has formerly made them poor candidates for clinical development because of difficulties in their production and purification. However, the results demonstrated in accordance with the present invention suggest the possibility that $IgG_3$ monoclonal antibodies can be used clinically because their cooperative and spontaneous aggregation provides a novel method for target linkage and activation of effector cells in a novel fashion. Unlike bifunctional monoclonals, the use of combinations of $IgG_3$ antibodies has distinct advantages: (1) flexibility in the delivery is possible, for example, the use of two $IgG_3$ antibodies allows the delivery of one antibody, which will localize on the chosen cell, followed by the delivery of the second agent which will localize on its respective cell and the subsequent association between the cells; and (2) the cost and difficulty of production and purification will be considerably lower.

Utilizing $IgG_3$ antibodies, novel biological therapies can be conducted. For example, $IgG_3$ antibodies to specific effector cells can be delivered in vivo once tumor cells have been pre-coated with other $IgG_3$ monoclonal antibodies and sufficient time is allowed for the clearance of the unbound circulating first antibody. In addition, other agents coupled to the mAb could be delivered to tumors that would activate effector cells upon their arrival. The effectiveness of this type of linkage could be altered or modified at both the effector and target cell level. We characterize this type of antibody binding as a cross-associational effect. We envision that the specificity of the immune cell can be retargeted or could be changed by appropriate administration of selected antibodies and/or biologicals.

Other antibodies than $IgG_3$'s are effective for use in accordance with the present invention. Many proteins are known to possess self-associative effects. In particular, there are large classes of known cryoglobulins in humans and other species that are expected to be useful as associational molecules in the present invention. As well, it is expected that associational effects can be built into an antibody, i.e., through the formation of hybrid antibodies that contain a chosen epitopic domain and an appropriate cross-associational domain.

Another example of an appropriate associational domain is the linking of biotin moiety to a first molecule that is specific for a binding region on a cell and linking of an avidin moiety that is specific for a binding region on another cell. For example, antibodies can be readily linked to biotin or avidin through techniques that are well known in the art. An antibody specific for an antigen on a tumor cell, linked with either biotin or avidin, can be administered to a patient with a tumor. The antibody will localize at the tumor cells. Concurrently, T-cells can be cultured and grown in culture and reacted with an antibody specific for a T-cell antigen that is linked with the complementary biotin or avidin which can then be administered to the patient. It will be understood that because of the high avidity of avidin for biotin (the associational constant of avidin for biotin is approximately $10^{15}$ or about one million times the avidity demonstrated by most antibody/antigen bonds), highly specific and strong associations can be formed between cells so associated.

Moreover, it will be appreciated that many other molecules can be similarly utilized as the associational molecule of the present invention. For example, it is expected that polymeric moieties can be prepared that possess associational properties. These moieties can be substituted for a heavy chain constant region on an antibody, or can be bound to other structural features, that recognize an epitope on, or are bound to, a cellular surface. This possibility has recently been demonstrated. Polymeric moieties have been shown to be capable of being "imprinted" to create selective recognition sites in polymers that function similarly to antibodies. This demonstration was made in ligand-binding assays for the drugs theophylline and diazepam. Mosbach et al. *Nature*, 361:645 (1993).

Other binding moieties, such natural ligands, cytokines, growth factors, and the like may also be substituted for the binding site of the antibody in selected cases. Through screening and/or protein engineering, synthetic or natural product ligands can also be identified.

Other associative domains may be contemplated than the $IgG_3$ $F_c$ region. It is known that some human cryoglobulins form a direct antibody-antibody association, which can be exploited in a similar manner. Also, other cryoglobulins of an IgM anti-IgG type (rheumatoid factor) can be useful. Further, some human myeloma proteins may be selected by screening for their self-aggregation property. These molecules would have the advantage of being less immunogenic in humans than some of the murine $IgG_3$ antibodies. Furthermore, other associative regions of low antigenicity can, in principle, be constructed using polymers or using naturally occurring binding regions.

The cross-associative effects of selected molecules may be altered or enhanced by variations in glycosylation, the presence of side chains of appropriate polarity, or addition of a third binding agent, e.g., an IgM anti-IgG rheumatoid factor.

II. PREPARATION AND CONSTRUCTION OF ANTIBODIES CONTAINING $IgG_3$ $F_c$ DOMAINS $IgG_3$ antibodies are particularly well suited for use in the present invention because of their demonstrated abilities to self-associate and cross-associate. Many IgG₃ antibodies that are specific for certain antigens are known in the art and are commercially available. For example, Table I provides a series of tumor specific $IgG_3$ antibodies that are known:

TABLE I

COMMON ANTI-TUMOR $IgG_3$ ANTIBODIES

| ANTIBODY | TUMOR CELL SPECIFICITY |
|---|---|
| 113F1 | breast, ovarian, and some colon cancers |
| NR-CO4 | colorectal cancers |
| R24γ₃ | melanoma GD3 antigen |
| 3F8 | melanoma GD2 antigen |
| 14.18 | melanoma GD2 antigen |
| 3F8 | neuroblastoma GD2 antigen |
| 14.18 | neuroblastoma GD2 antigen |
| BR96 | adenocarcinomas (Le' antigen) |
| 1E3 | ovarian and colon cancers |

With respect to effector cell, or lymphocytes, fewer $IgG_3$ antibodies are available. However, $R24_{\gamma 3}$ is an $IgG_3$ antibody with strong specificity for effector T-cells and has been produced by the National Cancer Institute and is available for clinical investigation. Also, it is expected that antibodies to the α, β, and CD3 polypeptide chains on the T-cell receptor of cytotoxic T-cells can be prepared with $IgG_3$ isotypes that should also be useful in the present invention. Antibodies to target antigens of other effector cells, such as granulocyte, Natural Killer (NK) eosinophil, and monocyte/ macrophage cells are expected to be useful in the present invention.

Moreover, it will be appreciated that class switching from IgM isotypes to $IgG_3$ isotypes can be accomplished. Abdel-moula et al. *J. Immunol.*, 143:526–532 (1989); Snapper et al. *J. Exp. Medicine*, 175:1367–1371 (1992); Snapper et al. *Immunology Today,* 14:15–17 (1993). Also using molecular engineering techniques, an $IgG_3$ version of any antibody, in principal, may be readily constructed. Thus, the numbers of possible antibodies of $IgG_3$ isotypes for any given cellular antigen is quite broad.

Antibodies for use in the present invention can be commercially obtained or can be specially prepared. Various techniques are well known in the art for the construction of antibodies that are specific for particular antigens. For example, hybridoma cell lines can be prepared that manufacture the chosen antibodies. Hybridomas are prepared according to conventional techniques. See, for example, Cohen et al., *J. Immunological Methods*, 117:121–129 (1989).

Experiment 1 Preparation of Antibodies

Mice of a chosen line (generally BALB/c mice) are immunized with small quantities of (i.e., 100 µg) of the chosen antigen that generally consists of materials from a column fraction containing the semi-purified antigen dissolved in PBS and mixed with Freund's complete adjuvant. The mixture (1:1) is injected interperitoneally. After a period of time (generally 7–30 days), the mice may be boosted with antigen mixed with incomplete adjuvant (1:1), with heat denatured antigen alone 1 week later, and then on three sequential days during the following week, after which the mice can be killed and the spleens removed.

The resulting spleen cells of the mice can be fused with a mouse myeloma line and hybridoma colonies can be established according to conventional techniques. E.g., Kennet et al., "Monoclonal Antibodies: Hybridomas: A New Dimension in Biological Analyses", Plenum Press, New York (1982). The resulting hybridoma colonies with the chosen antigen binding activity can be cloned at least four times by limiting dilution.

Colonies are then screened for specific antigen binding activity by ELISA, using small quantities (i.e., 100 µl) of hybridoma supernatant, using conventional techniques. E.g., Cohen et al., *J. Immunological Methods*, 117:121–129 (1989). From this screening, parental cell lines can be selected, with each parental cell line producing antibodies to the antigen complex. Each parental line can be grown to a density of approximately $10^6$ cells/ml in DMEM with 10% fetal calf serum (FCS) at 37° C. with 5% $CO_2$ in air in 75 $cm^2$ flasks with 10 ml of growth media in each. Medium can then be harvested after a week of growth and passed over a column (volume 2 ml) containing agarose coupled antibodies to murine IgG and IgM. The column was washed with 0.15M NaCl, then with 2 ml 0.05M glycine-HCl, pH 2.5, to elute the uncoupled antibodies from the column. The eluent, containing the antibodies, is neutralized and the solution was dialyzed against cold TRIS buffered saline (TBS; 0.02M TRIS/0.15M NaCl, pH 7.5).

Once hybridoma cell lines are prepared, monoclonal antibodies can be made through conventional techniques of priming mice with pristane and interperitoneally injecting such mice with the hybrid cells to enable harvesting of the monoclonal antibodies from ascites fluid.

Preferably, $IgG_3$ antibodies are prepared. However, as mentioned above, IgM antibody isotypes can be converted to $IgG_3$ isotypes. Generally, isotype switching from IgM to $IgG_3$ is accomplished by forming resting B-cell cultures that are αδ-dex-activated, sort purified membrane mIgM+ mIgG₃– and exposing the cells to γ-interferon in the presence of IL-5 (Snapper, et al. *J.Exp.Med.* 175: 1367–1371, 1992). It is not known whether this technique will work with IgM-producing hybridoma cells.

Experiment 2 Isotype Switching from IgM to $IgG_3$

A reliable technique to switch IgM- to $IgG_3$-producing hybridomas is a technique often referred to as Sib Selection. Hybridoma cells are washed and resuspended in serum-containing medium at a concentration of $10^4$ cells/ml. The cells are then plated at 1,000 cells/well into 10 96-well microtiter dishes. When the cells have grown, a sample of the supernatant fluid is tested for the presence of $IgG_3$ by a sensitive ELISA assay. The well which gives the strongest possible test is replated at 100 cells/well. The selection and replating is continued at 10 cells/well and then 1 cell/well. Often a feeder layer is required when the cell concentration is as low as 1 cell/well. The well with the strongest positive assay signal for $IgG_3$ is then grown and recloned at least twice.

In an alternative technique, $IgG_3$-producing hybridomas can be selected from IgM-producing hybridomas by cell sorting with a fluorescence activated cell sorter. Since isotype switched hybridomas will display $IgG_3$ on their surface, these cells can be identified and isolated using an FITC-conjugated goat anti-mouse $IgG_3$ specific reagent. It is important to clone any positive cells and test by a sensitive screening assay for the production of $IgG_3$.

Experiment 3 Recombinant Production of $IgG_3$ Hybrid Antibodies

Alternatively, preparation of antibodies containing the $IgG_3$ isotype can be accomplished by using recombinant DNA techniques also known as genetic engineering. This is an alternative method to obtain $IgG_3$ antibodies from hybridomas producing isotypes other than IgM. The molecular methodologies are performed as follows:

Initially, genomic DNA fragments containing the heavy and light chain variable region genes from the hybridoma producing the monoclonal antibody containing tumor or effector cell targeting activity are cloned. These techniques are well known to those of skill in the art. See, for example, Sun et al. *Proc. Nat'l Acad. Sci.*, 84:214–218 (1987); Steplewski et al. *Proc. Nat'l. Acad. Sci.*, 85:4852–4856 (1988). Thereafter, the genomic constant region genes from $IgG_3$-producing myelomas or other hybridomas shown to have self-associating properties are cloned. The nucleotide sequences for many $IgG_3$ isotypes are known. See, for example, Wels et al. *EMBO*, 3:2041–2046 (1984).

In each of the above steps, if the sequence of the genomic DNA is unknown, partial digestion of high molecular weight DNA of the cell lines with a restriction endonuclease and the separation of fragments by size, usually on agarose gels is accomplished. DNA fragments of appropriate sizes are packaged into phage particles (usually lambda phage) and recombinant plaques on *E. coli* are screened using established probes, if available, or cDNA probes produced from cytoplamsicm RNA from the hybridoma lines.

The ligation of the heavy and light chain variable region genes (of the hybridoma targeting either the tumor or effector cells) to the heavy and light chain constant region genes, respectively (of the $IgG_3$-producing cell line) can then be accomplished. This is accomplished by splicing at restriction sites and ligating into separate vectors or plasmids, which contain the necessary sequences for the expression of the introduced genes. Two plasmids are thus produced; one encoding the heavy chain variable and constant regions; and the other encoding the light chain variable and constant regions. In addition each plasmid contains a different drug-resistant marker.

The resulting plasmids are then transfected into immunoglobulin non-producing myeloma cells. This is done by the fusion of the *E. coli* protoplasts, containing both plasmids, to SP2/0 mouse myeloma cells. Transfected lines are selected in media containing both marker drugs.

Finally, the antibody produced by the transfected myeloma cell is carefully analyzed in order to discern isotype and specificity for the chosen target cell line. This should be done by a combination of biochemical, biophysical and biological assays. E.g., Steplewski et al. *Proc. Nat. Acad. Sci.*, 85:4852–4856 (1988); Sun et al. *Proc. Nat'l Acad. Sci.*, 84:214–218 (1987).

It will be appreciated that the portion of the antibody nearest the C-terminal from the hinge region is relatively irrelevant to antibody activity. Greenspan et al. *J. Immunol.*, 141:4276–4282 (1988), provided that the variance in the overall molecule's structural valence, segmental flexibility, and geometry, is not too great. Id. This fact indicates that antibodies wherein the heavy chain constant domain is altered to have an $IgG_3$ isotype will possess binding activity similar to the original antibody from which they are derived. However, such antibodies are expected to also possess the associational properties of $IgG_3$ isotypes.

III. ENHANCEMENT OF TUMOR CELL LYSIS THROUGH ASSOCIATIONAL EFFECTS

In the experiments discussed below, several antibodies that bind to effector cells and targets (target cell lines are shown in brackets) have been used: $R24_{\gamma 3}$, the $IgG_3$ reacting with a subset of T-cells and melanoma target cells [FeMX], but not colon cells; NR-CO4, an $IgG_3$ which reacts with colon tumors [LS180] and not with T-cells or melanomas. Control antibodies used in these experiments were: D612, an $IgG_{2\alpha}$ murine antibody which was not expected to participate in associative interactions with $IgG_3$ antibodies, but which does react with colon tumors [LS180]; and chimeric R24, an $IgG_1$ mouse-human chimeric version of the murine $R24_{\gamma 3}$, which reacts to the same antigens on T-cells and melanomas [FEMX], but is not expected to participate in $IgG_3$ type associative interactions.

These antibodies are categorized in Tables II and III.

TABLE II

Selected $IgG_3$ Antibody Reactivities with Tumor Cells Versus Lymphocytes

| ANTIBODY CLASS | TUMOR CELL REACTIVITY | LYMPHOCYTE REACTIVITY |
|---|---|---|
| R24 ($IgG_3$) | Melanoma Target Cell [FEMX] | Subset of T-Cells |
| NR-CO4 ($IgG_3$) | Colon Tumor Cells [LS180] No Reaction with Melanoma | No Reaction with T-Cells |

TABLE III

Control Antibodies That Do Not Participate In Tumor Antibody-Lymphocyte Antibody Association

| ANTIBODY CLASS | TUMOR CELL REACTIVITY | LYMPHOCYTE REACTIVITY |
|---|---|---|
| D612 (IgG2A) | Colon Tumor Cells [LS180] | None |
| R24 Chimeric (Mouse-Human IgG1) | Melanoma Target Cell [FEMX] | Same as $R24\gamma_3$ |

We have demonstrated in vitro that fresh human T cells, as well as cultured T cells, with or without $R24_{\gamma 3}$ for preactivation, can mediate a redirected non-MHC restricted lysis that is mediated by $IgG_3$ cooperative or self-aggregation. Significant lysis has been demonstrated using the LS-180 colon carcinoma target cell that lacks GD3 expression but expresses the antigen recognized by NR-CO4, another murine $IgG_3$ antibody. The combination of $R24_{\gamma 3}$ binding to the T cell and NR-CO4 binding to the tumor cell resulted in significant killing of LS-180 tumor cells.

The murine $R24_{\gamma 3}$ $IgG_3$ mAb cannot be replaced by the chimeric $ChR24_{\gamma 1}$ version of the $R24_{\gamma 3}$ (which lacks the inventive cooperativity), nor can the NR-CO4 be replaced by an mAb of the non-$IgG_3$ isotype (D612, $IgG_{2\alpha}$) directed against the colon target. Alteration in either part of the reaction resulted in a lack of binding and absence of subsequent activation of the lytic process.

The spontaneous aggregation of $IgG_3$ antibodies has formerly made them poor candidates for clinical development because of difficulties in their production and purification. However, these same qualities of $IgG_3$ that make it unsuitable for many uses are used in the present invention because the cooperative and spontaneous aggregation of $IgG_3$ provides a novel method for target linkage and activation of effector cells.

In our next experiment, we evaluated the potential of $R24_{\gamma 3}$ $F_c$-mediated aggregation between effector and target specific $IgG_3$ antibodies leading to tumor cell lysis. As the FeMX tumor cells also express the GD3 antigen, we were able to only use one associating antibody, $R24_{\gamma 3}$, in this experiment.

Experiment 4 $R24_{\gamma 3}$ Mediated Interaction of T cells and FeMX Tumor Cells Highly purified T-cells that were devoid of Natural Killer cells ("NK cells") were isolated as described below and used as the effector cells. Human peripheral blood mononuclear cells (PBMC) from normal donors were separated through conventional techniques on Ficoll-Hypaque density gradients. E.g., Garrido et al. *Cancer Research*, 50:4227–4232

(1990); Steplewski et al. *Proc. Nat. Acad. Sci.*, 85:4852–4856 (1988). Donors provided informed consent. Adherent cells (monocytes and B cells) were removed by incubation on plastic dishes and passaged through nylon wool columns. Highly enriched populations of CD3+CD56− T-cells (>98%) from PBMC were obtained by centrifugation of cells which passed through the nylon wool on discontinuous density gradients of Percoll (Pharmacia Fine Chemicals, Uppsala, Sweden).

Effector cells were identified as small resting T-cells [≧98% CD3+, ≦1% CD56+] and subsequently cultured for 3–5 days. Culture conditions were either a) in the absence of any additional stimuli; or b) in the presence of R24$_{\gamma 3}$, for preactivation (Table IV). Effector T-cells at a 100:1 ratio to FeMX tumor cells were used in a conventional 4-hour $^{51}$-Chromium release assay as previously described. E.g., Luzuy et al. *J. Immunol.*, 136:4420–4426 (1986). The Effector:Target ratio (E:T) values in Table IV represent percent specific release [±standard error].

As expected, a mixture of T cells and FeMX cells cultured in the absence of R24$_{\gamma 3}$ exhibited little or no cytotoxicity, whereas these cells precultured with R24$_{\gamma 3}$ demonstrated significant levels of cytotoxicity. In a control for this experiment, the addition of a rabbit polyclonal antiserum directed against FeMX (a rabbit polyclonal antibody used for antibody-dependent cellular cytotoxicity ("ADCC")) resulted in no cytotoxicity, indicating that no significant levels of cytotoxicity were being mediated by F$_c$ receptor positive effector cells.

When either the unstimulated cells or the activated T-cells (i.e., those pretreated with R24$_{\gamma 3}$ mAb) were subjected to an additional 10 μg/ml R24$_{\gamma 3}$ added into the assay mixture, a significant increase in basal cytotoxicity was observed. In addition, increased levels of cytotoxicity after R24$_{\gamma 3}$ activation were also evident. This increased lysis was consistent throughout all of the experiments performed.

TABLE IV

Effect of Additional R24$\gamma_3$ mAb on Killing of FeMX by T-Cells.

| E:T Ratio* | Control | | Pretreat with R24$\gamma_3$ | | ADCC + |
|---|---|---|---|---|---|
| | — | +R24$\gamma_3$ | — | +R24$\gamma_3$ | poly*** |
| 200 | 4 [1.5] | 18.5 [4] | 32 [3] | 44 [6] | 5 [2.5] |
| 67 | 3 [2] | 12 [3] | 13 [2] | 25 [1] | 6 [2] |
| 22 | 2 [1] | 2 [2] | 5 [1.5] | 10 [2.5] | 4 [3] |

*Values represent percent specific release ± standard error.
**Anisera used was a rabbit polyclonal anti-human sera that is used in ADCC with CD16 + effectors.

Figure 3:
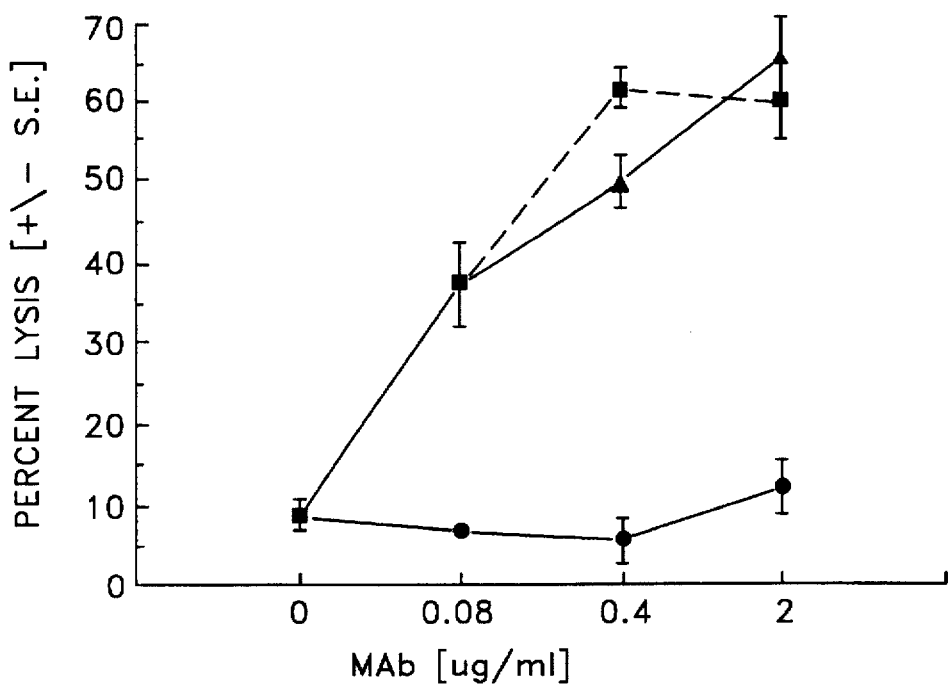
FIG. 3 is a line graph illustrating the effects of mAbs on non-MHC restricted T-cell cytotoxicity after culture. $IgG_3$ antibody $R24_{\gamma 3}$ targets an antigen (GD3) on melanoma cells and lymphocytes. $IgG_3$ antibody NR-CO4 targets an antigen on colon cancer cells but not on melanoma or lymphocytes. T-cells were cultured for 4 days with 50 µg/ml of $R24_{\gamma 3}$ mAb and were assayed against a FeMX cell melanoma target. The effector cells were present at a 100:1 ratio to $^{51}$-Chromium labeled tumor cells and were tested with addition of various concentrations of mAb $R24_{\gamma 3}$ alone (▲), mAb NR-CO4 (●) (control), or with a combination of both mAbs (■). A concentration dependent lysis of the FeMX tumor cells was evident in both the $R24_{\gamma 3}$ alone (▲), and mixture of $R24_{\gamma 3}$ and NR-CO4 (■). Values represent specific cytotoxicity±standard error [S.E.].

In addition, FIG. 3, graphically illustrates some of the results shown in Table IV. In FIG. 3, effector T-cells at a 100:1 ratio to $^{51}$-Chromium labeled FeMX tumor cells were incubated with various concentrations of mAb R24$_{\gamma 3}$ alone (▲), mAb NR-CO4 (●) (control), or with a combination of both mAbs (■). A concentration dependent lysis of the FeMX tumor cells was evident in both the R24$_{\gamma 3}$ alone (▲), and mixture of R24$_{\gamma 3}$ and NR-CO4 (■). There was no concentration dependent FeMX lysis illustrated when the cell mixture was incubated with only the NR-CO4 (●) antibodies. These results support our hypothesis that associating antibodies, specific for cell surface antigens, can cause lymphocyte mediated lysis of tumor cells. The NR-CO4 (●) antibody was not specific for either the tumor cells or T cells, and was therefore unable to stimulate cell lysis.

There were many possible interpretations of these data. One possibility was that homotypic aggregation between distinct R24$_{\gamma 3}$ IgG$_3$ molecules promoted bridging between the antibodies on the effector and target cells. Alternatively, it was possible that one R24$_{\gamma 3}$ epitopic domain on a single antibody molecule was binding to the effector cell, and the other epitopic domain was binding to the target cell, thus cross-linking the two cells. In order to further distinguish between all these alternatives, we performed a similar experiment using a combination of T cells and LS-180, a colon carcinoma cell line that was not reactive with the IgG$_3$ R24$_{\gamma 3}$ mAb. The LS-180 carcinoma cells are, however, reactive with the NR-CO4 IgG$_3$ antibody.

Experiment 5 Association of T cells With LS-180 Cells

Figure 4:
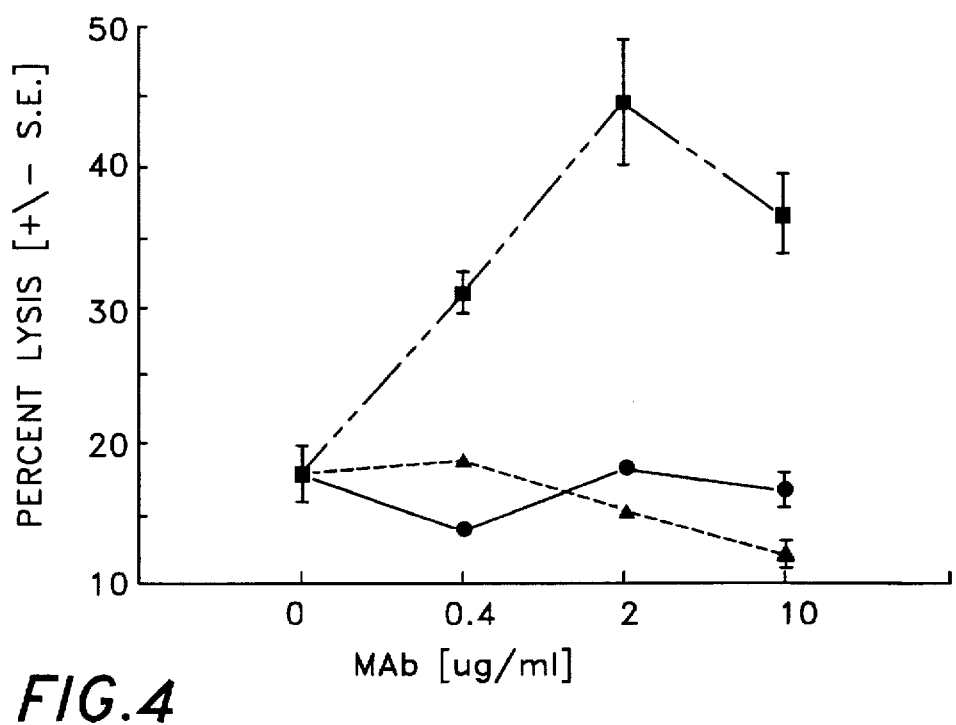
FIG. 4 is a line graph illustrating the results obtained by incubating LS-180 colon cancer target cells with T cells. The addition of both $R24_{\gamma 3}$ and NR-CO4 antibodies in combination (■) resulted in significant cytotoxicity. Addition of only $R24_{\gamma 3}$ (▲) or only NR-CO4 (●) did not cause increased cytotoxicity. Values represent specific cytotoxicity±standard error [S.E.].

T cells were prepared as discussed above. LS-180 carcinoma cells were $^{51}$-Chromium labeled. Results from a representative experiment (from more than a dozen) are shown in FIG. 4. We anticipated that when the R24$_{\gamma 3}$ antibodies bound to the T cells, and the NR-CO4 antibodies bound to the LS-180 cells, their IgG$_3$ regions would associate, leading to LS-180 cell lysis.

As hypothesized, referring now to FIG. 4, when LS-180 target cells were incubated with T cells, only the addition of both R24$_{\gamma 3}$ and NR-CO4 antibodies in combination (■) resulted in significant cytotoxicity. Addition of only R24$_{\gamma 3}$ (▲) or only NR-CO4 (●) did not result in increased cytotoxicity. We interpreted these results to demonstrate that the monoclonal IgG$_3$'s formed a F$_c$ region mediated aggregation. This aggregation let to effector and target cell binding through the antibodies' association domains. The binding of the activated T cells to the tumor cells thereafter stimulated T cell mediated LS-180 cell death, as measured by release of $^{51}$-Chromium.

In order to further elucidate the specificity of this reaction, the LS-180 target cell was studied with antibody combinations of either murine R24$_{\gamma 3}$ (IgG$_3$ isotype) or humanized chimeric R24 (human $_{\gamma 1}$ heavy chain isotype).

Experiment 6 Association of T cells and LS-180 Cells by Various Antibodies

As discussed above, chimeric antibodies can be constructed having a human constant region, and murine variable region. These types of chimeric antibodies can be made by various methods known to those with skill in the art.

Both murine IgG$_3$ R24$_{\gamma 3}$ antibody and humanized chimeric ChR24 (human $_{\gamma 1}$ heavy chain) have similar binding affinities, and stimulate T cells to a comparable extent, but differ in their F$_c$ regions. The ChR24 antibody was constructed by attaching the variable region of the murine R24$_{\gamma 3}$ antibody to the constant region from a human monoclonal antibody.

A representative experiment examining the effects of varying concentrations of both murine R24$_{\gamma 3}$ and human chimeric ChR24 antibodies on a mixture of T-cells and LS-180 cells is shown in Table V. As discussed previously, the addition of R24$_{\gamma 3}$ in combination with NR-CO4 resulted in significant levels of LS-180 cytotoxicity. When the ChR24 was substituted for the murine R24$_{\gamma 3}$ antibody, no cytotoxicity was noted, indicating that the murine IgG$_3$ was necessary to maintain the associational effect. Further, addition of anti-CD3 mAb (OKT3; IgG$_{2a}$) (specific for the T cell receptor complex) was unable to substitute for R24$_{\gamma 3}$. This result, again, demonstrates that IgG$_3$ antibody heavy chain constant regions are important for inducing the associational effect.

TABLE V

Comparison of Mouse Versus Chimeric R24 on Non-MHC Restricted Killing by T-cells.*

| Treatment | None | 10 | 1 | 0.1 |
|---|---|---|---|---|
| None | 5.5 [1.5] | | | |
| R24γ₃ | | 1.2 [1.5] | 0.5 [1.8] | −3.4 [1.3] |
| NR-CO4 | | 1.7 [1.3] | 1.6 [1.3] | 2.5 [1.0] |
| ChR24 | | −1.8 [1.2] | 1.5 [0.8] | −2.7 [1.7] |
| CD3 | | 0.6 [0.9] | 5.0 [2.0] | 3.2 [0.8] |
| R24γ₃+NR-CO4 | | 13.5 [1.2] | 6.3 [1.1] | 3.2 [1.1] |
| ChR24+NR-CO4 | | 0.5 [1.6] | −2.6 [0.3] | 1.5 [0.7] |
| CD3+NR-CO4 | | 0.5 [2.1] | 3.2 [1.2] | 0.1 [1.9] | mAb Dose μg/mL*

*Indicates final concentration of each antibody. mAb R24γ₃ (IgG₃) and chimeric human R24 (IgG₃) previously have been shown to react specifically with GD3 (8–10). Other antibodies used in these studies include: mAb NR-CO4 (IgG₃) and D612 (IgG₂ₐ) reacts with colon carcinoma. Control mAbs to CD3 (OKT3), CD16 (3G8) and mouse ascites (Ig) (control ascites, Life Technologies, Gaithersburg, MD) were used as measures of non-specific reactions.

Figure 5:
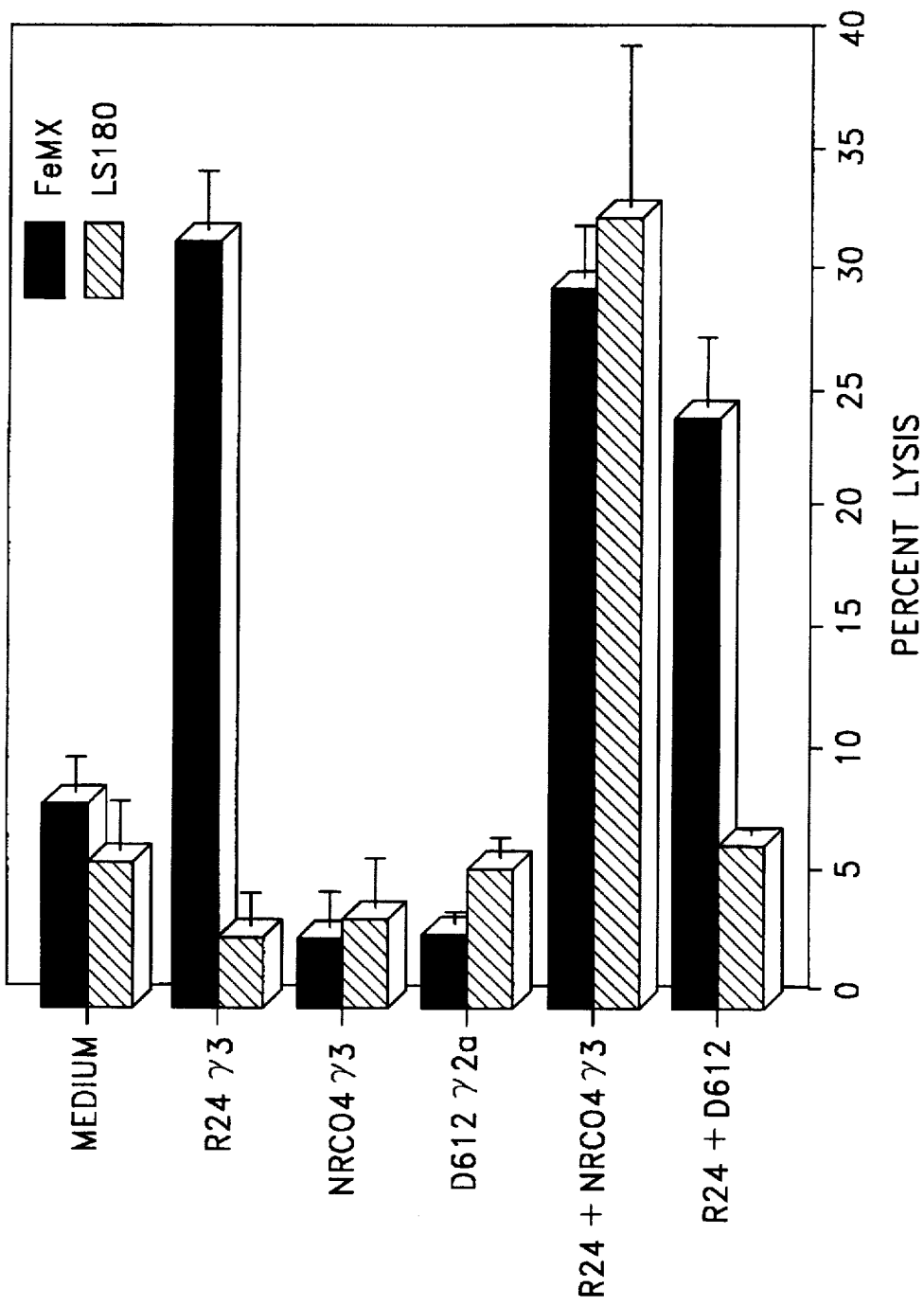
FIG. 5 is a bar graph depicting the levels of cytotoxicity when $IgG_3$ antibodies are used, compared to non-$IgG_3$ controls, against FEMX and LS-180 targets.

Finally, in an attempt to further prove the specificity of the association and reactions, an additional monoclonal antibody, D612 (an IgG$_{\gamma 2\alpha}$ that is reactive with the LS-180 target cell), was used. A representative experiment (of more than 4) is shown in FIG. 5.

As expected, using FeMX as the target cell, R24$_{\gamma 3}$ alone or in combination with any of the mAbs resulted in significant levels of cytotoxicity. When the LS-180 colon carcinoma target cell was used, the D612 IgG$_{2\alpha}$, which bound to LS-180, failed to induce lysis in the presence of R24$_{\gamma 3}$. Only R24$_{\gamma 3}$ in combination with the IgG₃ NR-CO4 resulted in significant cytotoxicity of LS-180. In data not shown, pretreatment of effector cells with R24$_{\gamma 3}$ mAb, and LS-180 cells with NR-CO4, followed by the removal of excess antibodies and subsequent co-culture also resulted in increased cytotoxicity. These results further indicate that cell-bound antibodies can cooperate in the proposed $F_c$—$F_c$ type activation.

These results are presented schematically in FIG. 6. In Panel A, both T cells and $^{51}$Chromium labeled FeMX cells were pretreated with R24$_{\gamma 3}$ antibodies. After washing away the excess antibodies in the media, the cells were incubated together. Even after removing the excess soluble antibodies, the T cells stimulated FeMX cell lysis. In Panel B (control), $^{51}$Chromium labeled LS-180 cells were incubated with NR-CO4 antibodies, and the T cells were pretreated without any antibodies. After rinsing the cells, there was no LS-180 cell lysis observed. In Panel C, the T cell was preincubated with R24$_{\gamma 3}$, while the $^{51}$Chromium labeled LS-180 cells were incubated with the non-IgG₃ antibody D612. There was no observed stimulation of LS-180 cell lysis using this combination. In Panel D, T cells were incubated with R24$_{\gamma 3}$ antibodies, and $^{51}$Chromium labeled LS-180 cells were preincubated with NR-CO4 antibodies. In this system, the IgG₃ domains on each antibody were able to associate and lead to LS-180 cell lysis.

Non-dose dependent response to the various antibodies are shown in the following Table IV.

TABLE VI

Comparative Effects of Monoclonal Antibodies to LS-180 Colon Cancer Cells and/or T-Cells

| Monoclonal Antibody Specific For Effector Cells | Monoclonal Antibody Specific For Tumor Target Cells | Percent Lysis of Tumor Target Cells |
|---|---|---|
| — | — | 8% |
| R24γ₃ | — | 9% |
| Chimeric R24 | — | 5% |
| — | NR-CO4γ₃ | 3% |
| — | D612γ₂ₐ | 5% |
| R24γ₃ | NR-CO4γ₃ | 22% |
| R24γ₃ | — | 7% |
| Chimeric R24 | | |
| R24γ₃ | D612γ₂ₐ | 8% |

Figure 7:
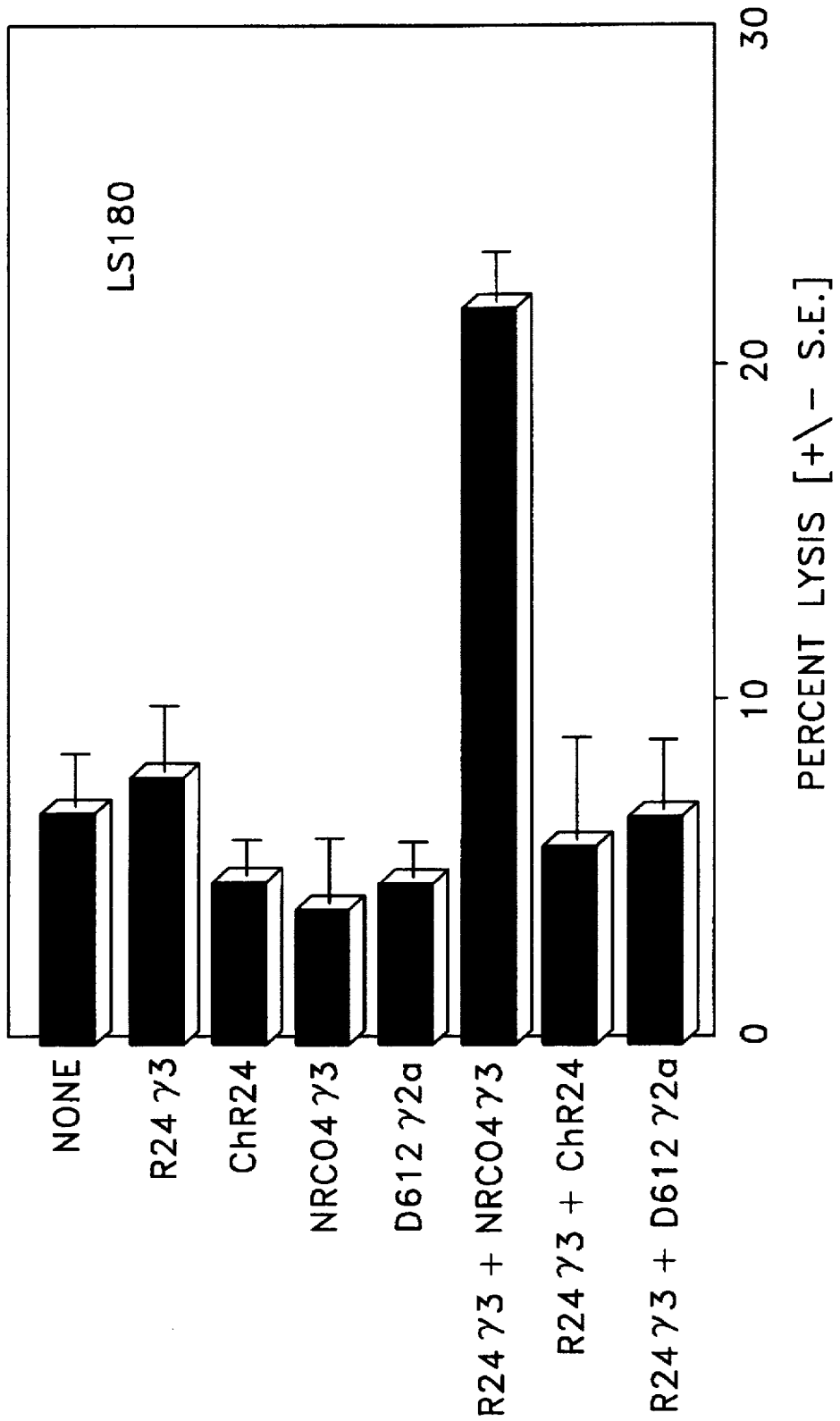
FIG. 7 is a bar graph illustrating the effects of various antibodies in a non-dose dependent manner on tumor cell lysis by T-cells.

The results from Table VI are shown as a bar graph in FIG. 7 illustrating the effects of the various antibodies in a non-dose dependent manner on tumor cell lysis by T-cells.

As recent studies have also demonstrated that freshly isolated T cells were capable of mediating non-MHC restricted cytotoxicity against B7 transformed cell line F815 (in the presence of anti-CD3 antibody), we examined whether the same effect might be found in this system using freshly isolated T cells.

Experiment 7 Cytotoxicity Using Fresh T cells

Figure 8:
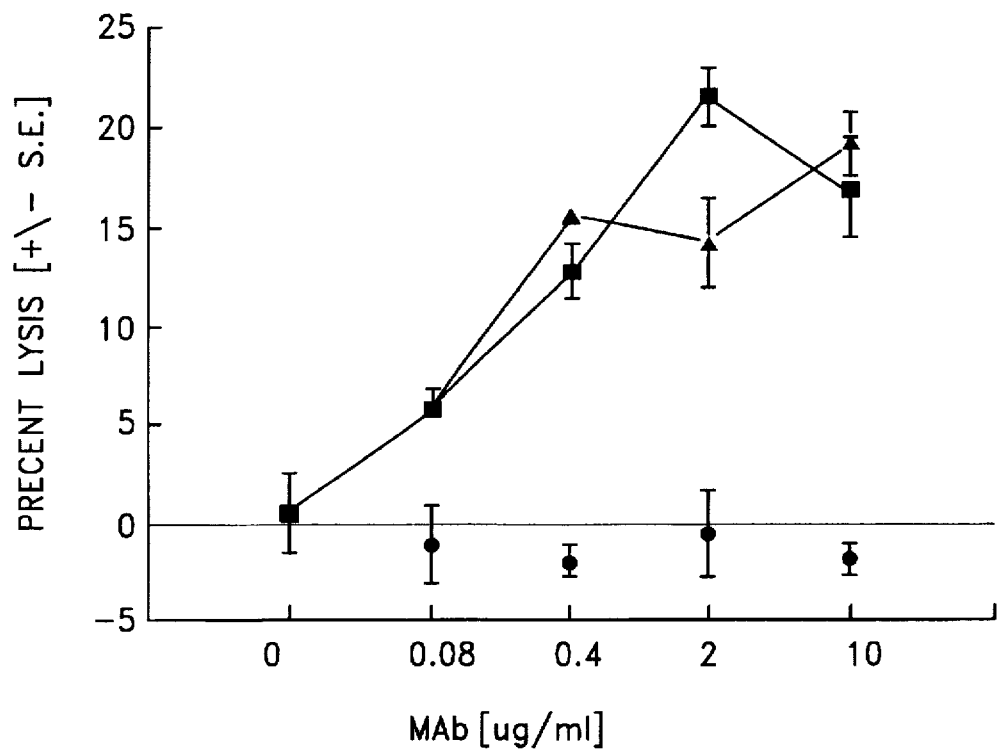
FIG. 8 is a line graph that illustrates typical results with a combination of T-cells and FeMX cells where the addition of $R24_{\gamma 3}$ alone (▲), or in combination with NR-CO4 (■), resulted in a dose-dependent activation of cytotoxicity that was absent in incubation of NR-CO4 alone (●).
Figure 9:
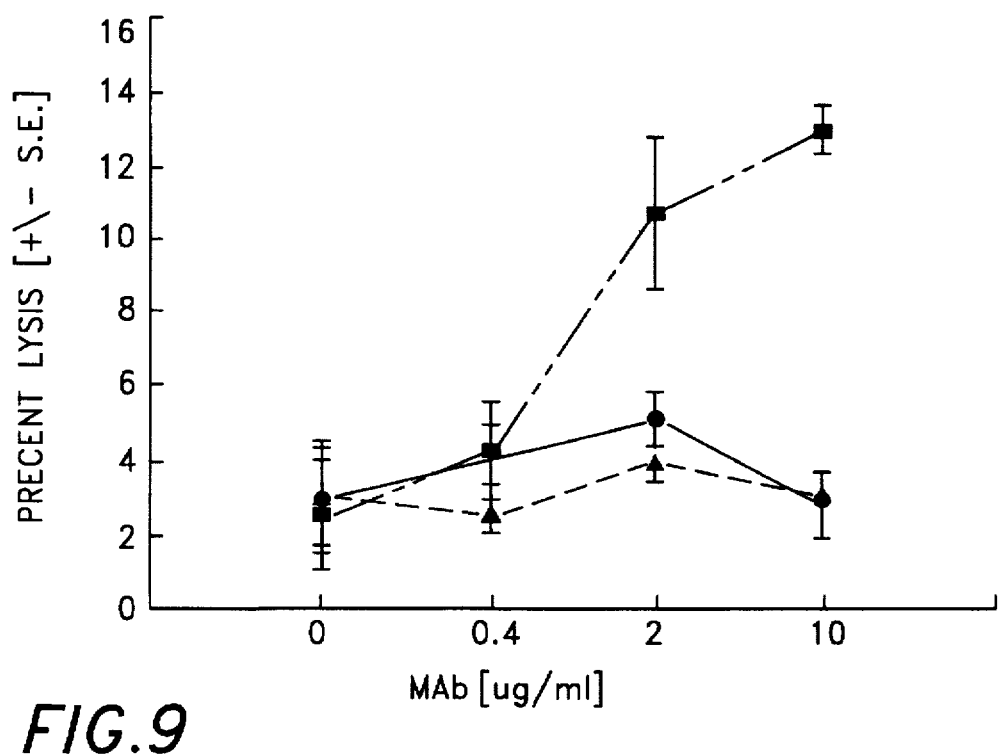
FIG. 9 is a line graph that illustrates the results of an experiment using fresh, uncultured T-cells and LS-180 carcinoma cells. Significant LS-180 cytotoxicity was found with fresh T-cells in the presence of both $R24_{\gamma 3}$ and NR-CO4 (■), while activation of cytotoxicity with $R24_{\gamma 3}$ alone (▲) or NR-CO4 alone (●) was absent.

Fresh T cells were isolated as described above. FIGS. 8 and 9 illustrate the results of a representative experiment wherein fresh T cells that had not been cultured or pretreated with any mAbs were tested for their ability to kill FeMX cells in vitro. When these effector cells were used, a similar pattern of cytotoxicity was seen compared with cells cultured and preactivated with R24$_{\gamma 3}$ mAb. FIG. 8 illustrates typical results with a combination of T cells and FeMX cells where the addition of R24$_{\gamma 3}$ alone (▲), or in combination with NR-CO4 (■), resulted in a dose-dependent activation of cytotoxicity that is absent in incubation of NR-CO4 alone (●).

FIG. 9 illustrates the results of an experiment using fresh T cells and LS-180 carcinoma cells. Significant LS-180 cytotoxicity can be seen with fresh T cells in the presence of both R24$_{\gamma 3}$ and NR-CO4 (■), while activation of cytotoxicity with R24$_{\gamma 3}$ alone (▲) or NR-CO4 alone (●) is absent. Other experiments (data not shown) have demonstrated that a 30 minute pretreatment of T cells with phorbol dibutyrate (presumably to activate their cytolytic machinery) can result in rapid and potent cytotoxicity exceeding 50% cell lysis. For these reasons, we believe that the associational method of triggering cytotoxicity can be exploited in freshly isolated T cells.

We will study the use of the associational molecules in vivo to determine whether a comparable tumor cell lysis could be invoked as a treatment for mammalian disease. One method of performing these treatments is described in the following experiment.

Experiment 8 Mouse In Vivo Therapeutic Use of Associational Antibodies

We have completed the first phase of our studies in vivo by demonstrating that IgG₃ antibodies to both melanoma and colon targets and an IgG₃ directed to GD3 on T cells in vitro can be targets for the inventive associational molecular binding that results T cell directed cytotoxicity. In one preferred therapeutic procedure, we follow the general protocol of stimulating T-cell production through the introduction of IL-2 or rIL-2 ("r" indicating recombinant) to a patient, followed by administration of an IgG₃ antibody to the tumor cell line. After waiting a period of time to allow clearing of the antibodies, the second, anti-T-cell antibody is intravenously administered.

Typically, we expect the method of the present invention to function similarly in vivo as the results described above in our in vitro studies. Consequently, tumor-bearing SCID or Nude (athymic) mice, which contain no mature T-cells will be injected through their intraperitoneal cavity. Injection with transferred human effector cells will be used in combination with various $IgG_3$ antibodies directed to tumor and effector cells to generate the desired cross-linking of antibodies and result in tumor cell lysis. For example, mice bearing tumors from the LS180 tumor cell line will be injected with (1) the effector cells alone; (2) effector cells with $R24_{\gamma 3}$ alone; (3) effector cells with NR-CO4 alone; or (4) the combination of $R24_{\gamma 3}$ and NR-CO4 with effector cells. Preferably, nude mice are used a model in order to eliminate any graft rejection by the host mouse.

The mice that receive either no antibody or only the antibody $R24_{\gamma 3}$ or NR-CO4, alone, will show little improvement in their condition (based on the tumor growth rate, tumor mass, and tumor incidence). In contrast, the mice injected with the combination of antibodies $R24_{\gamma 3}$ and NR-CO4 show significant improvement in their conditions, based upon the same factors.

This protocol, when repeated with the four groups of treatments described above will also be performed with and without various biologicals such as IL-1, IL-2, IL-3, IL-4, IL-5, IL-6, IL-7, IL-8, IL-9, IL-10, IL-11, IL-12, IL-13, Interferon-α, Interferon-β, Interferon-γ, granulocyte colony stimulating factor, granulocyte-macrophage colony stimulating factor, and monocyte colony stimulating factor to enhance the antitumor effectiveness of the transferred lymphocytes. It is expected that such molecules will enhance the rate of tumor cell lysis in the mice and aid in treating the tumors.

Where mice exhibit disseminated disease conditions from the spread of the tumor, intravenous, intradermal, and/or subcutaneous routes of inoculation of the tumor with intraperitoneal or intravenous inoculation of effector cells and antibodies can be used. It is expected that such administration will assist in eradicating the more widespread carcinomas.

Experiment 9 Human In Vivo Therapeutic Use of Associational Antibodies

It will be appreciated that in some instances, it is preferable to first grow the effector cell cultures in vitro. In such a case, the chosen effector cell line is separated as described above. The source of the effector cells may either be the patient upon whom therapy is to be conducted or another acceptable donor. The cells are cultured and stimulated as described above. See, for example, Steplewski et al. *Proc. Nat'l Acad. Sci.*, 85:4852–4856 (1988).

As will be appreciated, the choice of the effector cell depends on two conditions: (i) the choice of the antigen to which the first associating molecule or antibody is specific and (ii) the level of cytotoxicity exhibited by the effector cell on a given tumor cell. Appropriate effector cells generally include B-cells, T-cells, non-B or non-T cell lymphocytes, NK cells granulocytes, eosinophils, and monocyte/macrophages. The methods of isolating each of these effector cell types are well known in the art. Moreover, in respect of each effector cell type, there are a variety of stimulating factors that perform optimally with each. Such stimulating factors include IL-1, IL-2, IL-3, IL-4, IL-5, IL-6, IL-7, IL-8, IL-9, IL-10, IL-11, IL-12, IL-13, Interferon-α, Interferon-β, Interferon-γ, granulocyte colony stimulating factor, granulocyte-macrophage colony stimulating factor, and monocyte colony stimulating factor. The particularly preferred stimulating factor for each effector cell type chosen will be known to those of skill in the art.

When the cells have reached an acceptable density, e.g., $10^6$ cells/ml., they are ready for preparation for administration. At which time, the cells are treated with the appropriate T-cell associational molecule, i.e., an $IgG_3$ specific for the T-cells, such as $R24_{\gamma 3}$, or an engineered antibody or molecule with associational properties.

Alternatively, the effector cells may be first administered to the patient and the associational molecule specific for the T-cells can be administered to the patient concurrently, or at an appropriate later time.

The patient is administered a tumor specific antibody, specific for the tumor that he or she has developed. Thereafter, after the passage of sufficient time for unbound tumor directed antibody to clear, the prepared effector cells can be administered. The effector cells with the attached antibodies, will associate with the antibodies on the tumor cells, allowing the two cells to come into proximity. As has been demonstrated above, it is expected that the T-cells will cause a cytotoxic effect to the tumor cells and lead to a weakening of the tumor, if not a remission.

Experiment 10 Alternative In Vivo Therapeutic Use of Associational Antibodies

In another therapeutic procedure, a patient having a tumor is treated with an associating molecule, preferably an associating antibody, specific for the tumor cells. Concurrently or before, the patient is treated with an effector cell stimulating factor (i.e., IL-1, IL-2, IL-3, IL-4, IL-5, IL-6, IL-7, IL-8, IL-9, IL-10, IL-11, IL-12, IL-13, Interferon-α, Interferon-β, Interferon-γ, granulocyte colony stimulating factor, granulocyte-macrophage colony stimulating factor, and monocyte colony stimulating factor) in order to enhance the propagation of the chosen effector cells, such as B-cells, T-cells, non-B or non-T cell lymphocytes, NK cells, granulocytes, eosinophils, and monocyte/macrophages.

After the passage of sufficient time for any unbound first tumor specific antibody to clear, the patient is administered a second associational antibody specific for an epitope on the chosen effector cell that will associate with the associational domain on the first associational antibody.

It is expected that the effector cells with the attached antibodies, will associate with the antibodies on the tumor cells, allowing the two cells to interact. As has been demonstrated above, it is expected that the T-cells will cause a cytotoxic effect to the tumor cells and lead to a weakening of the tumor, if not a remission.

Experiment 11 Alternative Epitopic Associational Molecules

Alternative association molecules are appropriate with a number of different target epitopes. In the first case, alternative effector cell targeting antibodies can be created. For example, instead of using antibodies specific for the GD3 antigen on lymphoid effector cells, antibodies to the integrins (CD18, LFA1), antibodies to triggering receptors on NK cells and on neutrophils (such as CD16), triggering molecules on macrophages, and NK cells (such as the CD11c (C3bI) receptor) or triggering molecules on T-cells, such as the CD3 molecules are prepared. Antibodies of the $IgG_3$ subclass to all of these molecules may be used in order to trigger the various effector cell subsets.

It is expected that both in vitro and in vivo binding of cells bound with these above discussed antibodies to tumor cells that are coated with another $IgG_3$, with the NR-CO4 being the model system, will exhibit similar strength and cytotoxic potential. Various combinations of triggering molecules on macrophage, neutrophil, NK cell, and T-cell effectors can be used for in vivo experiments with a series of monoclonals IgG$_3$ effector-specific reagents would be administered in vivo. This would serve to harness a variety of immune effector cells at or near the tumor site, in an attempt to eradicate tumor presence.

Experiment 12 Enhanced Alternative Associational Molecules

Another example of an appropriate associational domain is the linking of biotin moiety to a first molecule that is specific for a binding region on a cell and linking of an avidin moiety that is specific for a binding region on another cell. For example, antibodies can be readily linked to biotin or avidin through techniques that are well known in the art. An antibody specific for an antigen on a tumor cell, linked with either biotin or avidin, can be administered to a patient with a tumor. The antibody will localize at the tumor cells. Concurrently, T-cells can be cultured and grown in culture and reacted with an antibody specific for a T-cell antigen that is linked with the complementary biotin or avidin which can then be administered to the patient. It will be understood that because of the high avidity of avidin for biotin (the associational constant of avidin for biotin is approximately $10_{15}$ or about one million times the avidity demonstrated by most antibody/antigen bonds), highly specific and strong associations can be formed between cells so associated.

What we claim is:

1. A method for associating cells, comprising:

contacting and binding a first IgG3 antibody specific to a first antigen on a first cell to said first cell to form a first IgG3-cell pair;

contacting and binding a second IgG3 antibody specific to a second antigen on a second cell to said second cell under in vitro conditions to form a second IgG3-cell pair, said second antigen being antigenically different from said first antigen; and exposing said first IgG3-cell pair to said second IgC3-cell pair, wherein said first and second IgG3-cell pairs become non-covalently associated via their $F_c$ regions.

2. The method of claim 1, wherein said first and second cells are associated in vitro.

3. The method of claim 1, wherein each of said first and second antibodies are murine IgG$_3$ antibodies.

4. The method of claim 1, wherein the first cell is a tumor cell.

5. The method of claim 1, wherein the second cell is an effector cell.

6. The method of claim 5, wherein the effector cell is selected from the group consisting of granulocytes, B-cells, NK cells, T-cells, non-B cell lymphocytes, non-T cell lymphocytes, eosinophils, and macrocyte/macrophages.

7. The method of claim 6, wherein the effector cell is a T-cell.

8. The method of claim 1, wherein an equimolar ratio of the first associating antibody and the second associating antibody are employed.

9. The method of claim 1, wherein a non-equimolar ratio of the first associating antibody and the second associating antibody are employed.

10. A method for associating cells, comprising:

contacting and binding a first IgG3 antibody to a first cell, said first antibody having a first antigen combining site and a first $F_c$ region; and contacting and binding a second IgG3 antibody to a second cell, said second antibody having a second antigen combining site different from said first antibody and having a second $F_c$ region, wherein said first $F_c$ region and said second $F_c$ region associate non-covalently to bring said first and second cell in proximity.

11. The method of claim 10, wherein said first and second cells are associated in vitro.

12. The method of claim 10, wherein each of said first and second antibodies are murine IgG$_3$ antibodies.

13. The method of claim 10, wherein the first cell is a tumor cell.

14. The method of claim 10, wherein the second cell is an effector cell.

15. The method of claim 14, wherein the effector cell is selected from the group consisting of granulocytes, B-cells, T-cells, non-B cell lymphocytes, non-T cell lymphocytes, eosinophils, and macrocyte/macrophages.

16. The method of claim 15, wherein the effector cell is a T-cell.

17. The method of claim 10, wherein an equimolar ratio of the first associating antibody and the second associating antibody are employed.

18. The method of claim 10, wherein a non-equimolar ratio of the first associating antibody and the second associating antibody are employed.

19. A method of facilitating effector cell-directed tumor cell death in a mammal, comprising:

administering a first IgG3 antibody specific for a tumor cell antigen to said mammal, said first IgG3 antibody having a first $F_c$ region; and administering a second IgG3 antibody specific for a cytotoxic effector cell antigen different from said tumor cell antigen to said mammal, said second antibody having a second $F_c$ region, wherein the first and second $F_c$ regions interact non-covalently to bring said tumor cell in proximity to said effector cell, thereby facilitating cytotoxic effector cell action on said tumor cell.

20. The method of claim 19, wherein each of said first and second antibodies are murine IgG$_3$ antibodies.

21. The method of claim 19, wherein the effector cell is selected from the group consisting of B-cells, T-cells, non-B cell lymphocytes, non-T cell lymphocytes, NK cells, granulocytes, eosinophils, and monocyte/macrophages.

22. The method of claim 21, wherein said effector cell is a T-cell.

23. The method of claim 19, wherein an equimolar ratio of the first antibody and the second antibody are employed.

24. The method of claim 19, wherein a non-equimolar ratio of the first antibody and the second antibody are employed.

25. The method of claim 19, wherein prior to administering said second antibody, the method further comprises the additional step of administering an effector cell stimulating factor under conditions that will promote the growth and propagation of effector cells.

26. The method of claim 25, wherein said effector cell stimulating factor is selected from the group consisting of IL-1, IL-2, IL-3, IL-4, IL-5, IL-6, IL-7, IL-8, IL-9, IL-10, IL-11, IL-12, IL-13, Interferon-α, Interferon-γ, Interferon-γ, granulocyte colony stimulating factor, and monocyte colony stimulating factor.

27. A method to facilitate effector cell-directed tumor cell death in a patient having a tumor with a tumor cell antigen, comprising:

isolating and separating cytotoxic effector cells from the patient;

culturing said effector cells under conditions that will promote the propagation of said effector cells;

administering a first antibody to the cytotoxic effector cell culture to the patient, said antibody having affinity for said cytotoxic effector cells and additionally possessing a first $F_c$ region;

administering to the patient a second antibody specific for the tumor cell antigen in the patient, said second antibody having a second $F_c$ region; and administering to said patient the cultured effector cells, wherein the first and second $F_c$ regions interact to bring said tumor cells in proximity to said effector cells, thereby facilitating cytotoxic effector cell action on said tumor cells.

28. A method of facilitating effector cell-directed tumor cell death in an animal with a tumor, comprising:

administering to the animal a first antibody with an $IgG_3$ isotype heavy chain constant region having a variable region that is specific for the tumor; and administering a second antibody which specifically binds ganglioside $G_{D3}$ on the effector cell to the animal.

* * * * *